(12) United States Patent
Hoener et al.

(10) Patent No.: US 7,399,900 B2
(45) Date of Patent: Jul. 15, 2008

(54) NEMATODES AS MODEL ORGANISMS FOR THE INVESTIGATION OF NEURODEGENERATIVE DISEASES, IN PARTICULAR PARKINSONS DISEASE, USES AND METHODS FOR THE DISCOVERY OF SUBSTANCES AND GENES WHICH CAN USED IN THE TREATMENT OF THE ABOVE DISEASE STATES AND IDENTIFICATION OF ANEMATODE GENE

(75) Inventors: Marius Hoener, Basel (CH); Giuseppe Cassata, München (DE); Wolfgang Link, Madrid (ES); Ralf Baumeister, Gröbenzell (DE); Karlheinz Tovar, Alling (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 555 days.

(21) Appl. No.: 10/239,249

(22) PCT Filed: Mar. 21, 2001

(86) PCT No.: PCT/EP01/03214

§ 371 (c)(1),
(2), (4) Date: Apr. 4, 2003

(87) PCT Pub. No.: WO01/70944

PCT Pub. Date: Sep. 27, 2001

(65) Prior Publication Data

US 2003/0177507 A1    Sep. 18, 2003

(30) Foreign Application Priority Data

Mar. 22, 2000   (DE) ................ 100 14 109

(51) Int. Cl.
*A01K 67/00*     (2006.01)
*A01K 67/033*   (2006.01)
*C12N 15/00*    (2006.01)
*C12N 5/00*     (2006.01)

(52) U.S. Cl. ............ 800/8; 800/3; 800/9; 800/13; 800/21; 435/69.1; 435/320.1; 435/325; 435/455

(58) Field of Classification Search ............ None
See application file for complete search history.

(56) References Cited

U.S. PATENT DOCUMENTS 5,196,333 A   3/1993 Chalfie et al. ............ 435/240.1

FOREIGN PATENT DOCUMENTS

| EP | 0908 727 A1 | 4/1999 |
|---|---|---|
| EP | 1063 294 A1 | 12/2000 |
| WO | WO 96/25946 | 8/1996 |
| WO | WO 98/53856 | 12/1998 |
| WO | WO 98/59050 | 12/1998 |
| WO | WO 00/63427 | 10/2000 |

OTHER PUBLICATIONS

Link, Mech Ageing Dev. 122(14):1639-49, 2001.*
Nass et al, Parkinsonism Relat Disord. (3):185-191. 2001.*
Springer et al, Caenorhabditis elegans Parkin mutant with altered solubility couples alpha-synuclein aggregation to proteotoxic stress. Hum Mol Genet. 14(22):3407-3423,2005.*
Polymeropoulos, M.H. et al., "*Mutation In The Alpha-Synuclein Gene Identified In Families With Parkinson's Disease*," Science (276):2045-7 (1997).
Kitada, T. et al., "*Mutations In The Parkin Gene Cause Autosomal Recessive Juvenile Parkinsonism,*" Nature (392):605-8 (1998).
Baumeister, R. et al., "*Lineage-specific Regulators Couple Cell Lineage Asymmetry To The Transcription Of The Caenorhabditis Elegans POU Gene Unc-86 During Neurogenesis*," Genes Dev. (10):1395-1410 (1996).
Way, J.C. et al., "*The MEC-3 Gene Of Caenorhabditis Elegans Requires Its Own Product For Maintained Expression And Is Expressed In Three Neuronal Cell Types*," Genes Dev. (3):1823-1833 (1989).
Hobert, O. et al., "*Regulation Of Interneuron Function In The C. Elegans Thermoregulatory Pathway By The TTX-3 LIM Homeobox Gene*," Neuron (19):345-57 (1997).
Dunnett, S.B. et al., "*Prospects For New Restorative And Neuroprotective Treatments In Parkinson's Disease*," Nature (399S):A32-A39 (1999).
Hattori, N. et al., "*Molecular Genetic Analysis Of A Novel Parkin Gene In Japanese Families With Autosomal Recessive Juvenile Parkinsonism: Evidence For Variable Homozygous Deletions In The Parkin Gene In Affected Individuals*," Ann. Neurol. (44):935-941 (1998).
Liu, L.X. et al., "*High-Throughout Isolation Of Caenorhabditis Elegans Deletion Mutants*," Genome Res. (9):859-867 (1999).
Olanow, C.W. et al., "*Etiology And Pathogenesis Of Parkinson's Disease*," Annu. Rev. Neurosci. (22):123-144 (1999).
Yandell, M.D. et al., *Trimethylpsoralen Induces Small Deletion Mutations In Caenorhabditis Elegans*, Proc. Natl. Acad. Sci. (91):1381-1385 (1994).
Clayton, D.F. et al., "*The Synucleins: A Family Of Proteins Involved In Synaptic Function, Plasticity, Neurodegeneration And Disease*," TINS (21):249-254 (1998).
Glasson, B.I. et al., *A Hydrophobic Stretch Of 12 Amino Acid Residues In The Middle Of Alpha-Synuclein Is Essential For Filament Assembly*, J. Biol. Chem. (276):2380-2386 (2001).

(Continued)

*Primary Examiner*—Sumesh Kaushal

(57) ABSTRACT

The invention relates to nematodes as model organisms for the investigation of neurodegenerative diseases in particular. Parkinsons disease, uses and methods for the discovery of substances and genes which can be used in the treatment of the above disease states and identification of a nematode gene, from *C. elegans*, which is homologous to the human parkin gene associated with Parkinsons disease. The invention further relates to those nematodes which contain an aberrant or missing expression of at least one gene, preferably a parkin gene and/or a α-synuclein gene, which is connected with Parkinsons disease. According to the invention, the above organisms can be used for the identification and characterisation of medicaments for the treatment of said disease states.

9 Claims, 11 Drawing Sheets

OTHER PUBLICATIONS

Feany, M.B. et al., "*A Drosophila Model of Parkinson's Disease*," Nature (404):394-398 (2000).

Finney, M. et al., "*The Unc-86 Gene Product Couples Cell Lineage and Cell Identity in C. Elegans*," Cell (63):895-905 (1990).

Kruger, R. et al., *Ala30Pro Mutation In The Gene Encoding Alpha-Synuclein In Parkinson's Disease*, Nat. Genet. (18):106-8 (1998).

Masliah, E. et al., *Dopaminergic Loss And Inclusion Body Formation In Alpha-Synuclein Mice: Implications For Neurodegenerative Disorders*, Science (287):1265-1269 (2000).

Mello, C.C. et al., "*Efficient Gene Transfer in C. Elegans. Extrachromosomal Maintenance And Integration Of Transforming Sequences*," EMBO J. (10):3959-3970 (1991).

Okochi, M. et al., "*A Loss Of Function Mutant Of The Presenilin Homologue SEL-12 Undergoes Aberrant Endoproteolysis In Caenorhabditis Elegans And Increases A$\beta$42 Generation In Human Cells*," J. Biol. Chem. (275):40925-32 (2000).

Zamore, P.D. et al., *RNAi: Double-Stranded RNA Directs The ATP-Dependent Cleavage of mRNA at 21 To 23 Nucleotide Intervals*, Cell (101:25-33 (2000).

Baumeister R. et al., "*Human Presenilin-1, But Not Familial Alzheimer's Disease (FAD) Mutants, Facilitate Caenorhabditis Elegans Notch Signalling Independently Of Proteolytic Processing*," Genes and Function (1):149-159 (1997).

\* cited by examiner

FIG. 3

Parkin cDNA derived from C. *elegans*, coding region.

```
atgtctgatgaaatctctatattaatacaagatagaaaaacaggtcaacgtaggaatctaacacttaatataaata
taactggaaatatcgaagatctcacaaaagatgtggaaaagctcaccgaaattcccagcgatgagctggaagtggt
tttctgtgggaaaaagttatcaaaatcaacgattatgagggatttgtcactgacacctgcaacacaaatcatgctt
ctccgtccaaagttcaatagtcacaacgaaaacggtgctactactgcaaaaataacaacagattcttcaattctcg
gaagcttctacgtgtggtgcaaaaattgtgacgacgtcaagcgcggcaaactgcgggtttattgccaaaaatgctc
gtcaacctctgttctagtcaaatctgaacccagaactggtccgacgttctcaaaagcaagagaataccggcggtc
tgcgaagaatgctgtactccaggtcttttcgctgaattcaagttcaaatgtctagcctgcaacgatccggccgcag
ctctaactcacgtacgcggaaattggcaaatgaccgagtgctgtgtttgtgatgggaaggagaaagtgatcttcga
cctcggatgcaatcatattacatgccaattctgtttcagaGATTATTTGCTAAGTCAACTGGAACGATTCGGTTTT
GTCAATCAGCCGCCGCATGGCTTCACCATTTTCTGCCCCTATCCAGGGTGCAATAgagtggtacaagatgtgcacc
atttccacattatgggtcagacgtcgtacagcgaataccaacggaaagccaccgagcgattgattgccgtggacga
caagggtgtgacttgcccgaatgtctcgtgtgggcagagcttcttctgggagccctatgatgacgatggaagatcc
cagtgtccagattgttttttttcgttttgcagaaagtgcttcgaaagaaattgtgtgtgccagagcgaagacgatc
tcacccgaactacaattgacgcgactacaagaagatgcccaaaatgccacgtggcaaccgaacggaacggcggatg
tgctcacattcactgtacctcgtgtggaatggattggtgtttcaagtgcaagacagaatggaaggaagagtgtcaa
tgggaccattggtttaattaa
```

Derived amino acid sequence of C *elegans*, Parkin

```
MSDEISILIQDRKTGQRRNLTLNINITGNIEDLTKDVEKLTEIPSDELEVVFCGKKLSKSTIMRDLSLTPATQIML
LRPKFNSHNENGATTAKITTDSSILGSFYJWCKNCDDVKRGKLRVYCQKCSSTSVLVKSEPQNWSDVLKSKRIPAV
CEECCTPGLPAEFKFKCLACNDPAAALTHVRGNWQMTECCVCDGKEKVIFDLGCNHITCQFCFRDYLLSQLERFGF
VNQPPHGFTIFCPYPGCNRVVQDVEHFHIMGQTSYSEYQRKATERLIAVDDKGVTCPNVSCGQSFFWEPYDDDGRS
QCPDCFFSFCRKCFERNCVCQSEDDLTRTTIQATTRRCPKCHVATERNGGCAHIHCTSCGMDWCFKCKTEWKEECQ
WDHWFN
```

FIG. 4a: Expression of GFP under the control of 4085 bp of the Parkin promoter
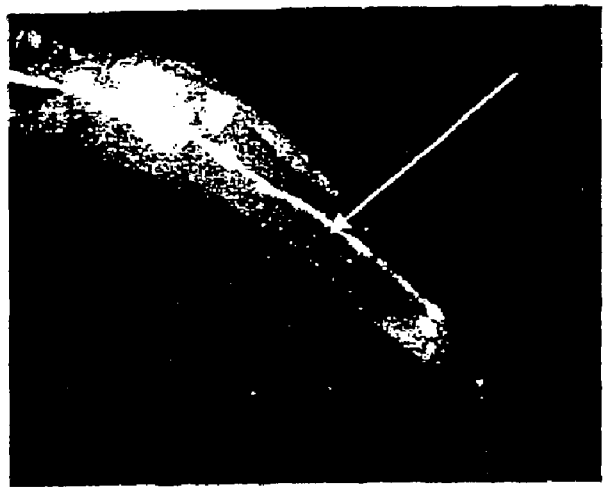
Expression in neurons in the posterior region of C. elegans.
Arrow: ventral nerve cord axons
Expression in all the cells of the pharynx
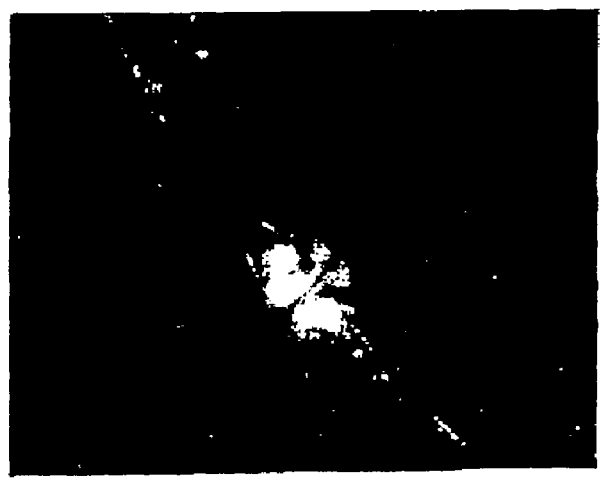
Expression in all the cells of the vulva ← Normal stage at which eggs are laid (gastrulation)

← Morphogenesis (bean stage)

High molecular weight aggregates of α-synuclein in C. elegans

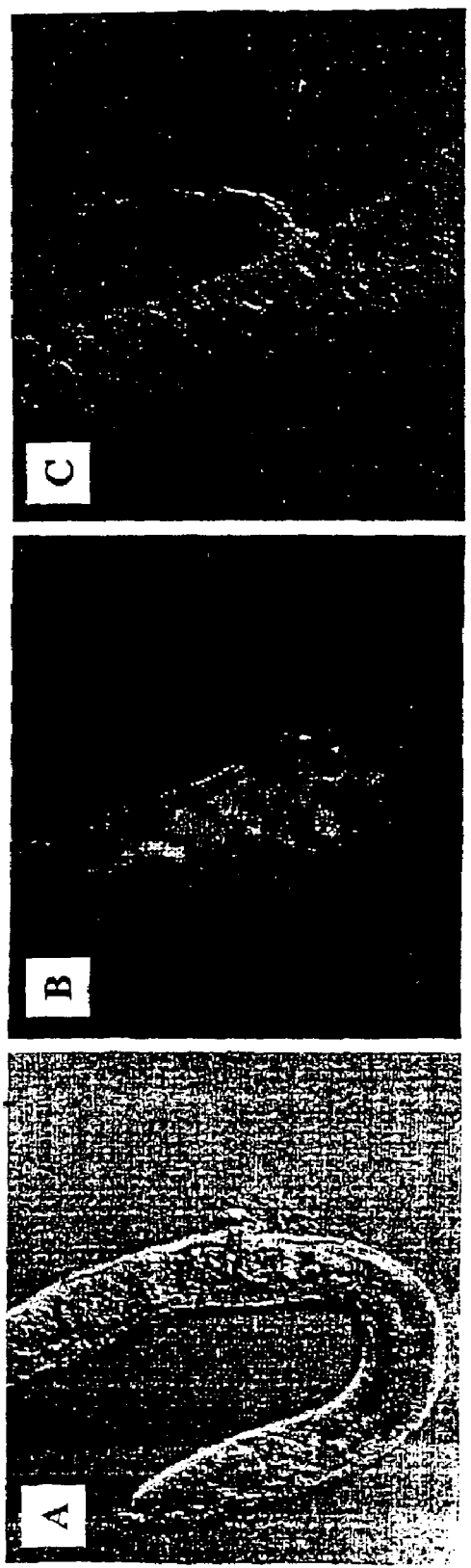
Figure 12. Expression of α-synuclein in *C. elegans* causes a defect in egglaying and deformation of the vulva

NEMATODES AS MODEL ORGANISMS FOR THE INVESTIGATION OF NEURODEGENERATIVE DISEASES, IN PARTICULAR PARKINSONS DISEASE, USES AND METHODS FOR THE DISCOVERY OF SUBSTANCES AND GENES WHICH CAN USED IN THE TREATMENT OF THE ABOVE DISEASE STATES AND IDENTIFICATION OF A NEMATODE GENE

The invention relates to nematodes as model organisms for investigating neurodegenerative diseases, and, in particular, Parkinson's disease, which nematodes can be used for developing pharmaceuticals for treating neurodegenerative diseases, including those diseases in which plaque-like deposits (amyloidoses) occur, and, in particular, for treating Parkinson's disease.

The animal model according to the invention is based on a gene which is connected to the development of Parkinson's disease either being expressed in an aberrant manner, or not being expressed at all, in a nematode.

An animal model of this nature can also be used for clarifying the metabolic pathways and for identifying new genes which are involved in Parkinson's disease.

BACKGROUND OF THE INVENTION

Transgenic animal models are already available, as valuable tools for clarifying disease processes and identifying and characterizing pharmaceuticals which have a prophylactic or therapeutic effect, for a variety of disease types. The prerequisite for developing such animal models is, in particular, knowledge of genes which are involved in the given disease processes.

Aside from Alzheimer's disease, Parkinson's disease is the most well known disease in the neurodegenerative disease group. It is characterized by (1) a slowing down of all movements (bradykinesia), quiet and monotonous speech (akinesia or hypokinesia), absence of the physiological associated movements, a stooped posture, a small-step, partially shuffling gait, handwriting which becomes smaller as the writing continues, uncontrollable disturbances in movement, with a tendency to fall forward to the side or backward, (2) rigidity of the musculature (rigor), and (3) coarse resting tremor (trembling). Parkinson's disease is a disease which occurs relatively frequently and develops in approx. 1% of individuals aged over 60, in particular in men. The disease is caused by loss of dopamine in the striatum, resulting in the degeneration of neurons in the substantia nigra. The primary reason for loss of dopamine is not known (Dunnett and Björklund, 1999; Olanow and Tatton, 1999). Although the appearance of Parkinson's disease is sporadic as far as most patients are concerned, there is a small group of patients in whose families the disease occurs frequently. Molecular-genetic analyses performed in these families have led to the identification of several genes which, having been altered by mutations, are causatively involved in the onset of Parkinson's disease. One of these genes, which was discovered in 1998 by Nobuyoshi Shimizu, Yoshikuni Mizuno and their coworkers, has since then been designated Parkin or PARK2 (Kitada et al., 1998; Hattori et al., 1998). This gene was found to be mutated in several families in which several family members had developed autosomal recessive juvenile (beginning before the 40th year of life) Parkinson's disease. The protein of the Parkin gene is characterized, inter alia, by an ubiquitin domain in the N terminus, two RING finger-like motifs in the C terminus and an IBR (in between ring fingers) domain.

Another gene which has also been identified as being causatively involved in Parkinson's disease is the a-synuclein gene (Polymeropoulos et al., 1997). α-Synuclein is found, in particular, in the fibrillary, intracytoplasmic inclusions (Lewy bodies) which appear in association with Parkinson's disease. Aside from the presynaptic protein a-synuclein, a large number of proteins, such as ubiquitin and neurofilament are also represented in the Lewy bodies. Mutations (A53T and A30P) in the α-synuclein gene on human chromosome 4q21-q22 lead to an autosomally dominant form of Parkinson's disease (Polymeropoulos et al., 1997; Kruger et al., 1998). How these mutations are able to induce Parkinson's disease has still not been elucidated. The dominant inheritance pattern and the fact that α-synuclein is present in Lewy bodies in fibrillary aggregations whose formation can be accelerated by the two mutations points to toxicity as the mechanism (toxic gain of function). A recent study has identified a sequence of 12 amino acids in the middle of α-synuclein which is responsible for the aggregation in vitro and which is absent from the very similar protein β-synuclein, which is nonaggregating (Giasson et al., 2000). α-Synuclein has thus far only been identified in vertebrates, with threonine, instead of alanine, as is the case in humans, being found in position 53 of the amino acid sequence in all the species known to date (Clayton and George, 1998).

Transgenic animal models which express different variants of human α-synuclein have thus far been established in the mouse and in Drosophila. The neuronal expression of α-synuclein in the mouse leads to a progressive accumulation of α-synuclein in intraneuronal inclusions, which inclusions are not, however, of a fibrillary nature (Masliah et al., 2000). By contrast, transgenic flies, which express α-synuclein panneuronally, exhibit fibrillary inclusions, which resemble the Lewy bodies, a loss of dopaminergic neurons and impairment of locomotory functions (Feany and Bender, 2000). In this connection, there were no significant differences in the expression of the individual forms of α-synuclein (wt, A53T and A30P).

SUMMARY OF THE INVENTION

As compared with the animal models for Parkinson's disease which have already been published, the advantages of a nematode model, in particular of the C. elegans model, are, in particular, its suitability for a high-throughput method (high-throughput screening) (HTS), the possibility of being able to carry out a genetic analysis more rapidly as a result of a shorter generation time (2-3 days, as compared with weeks in the case of Drosophila) and detailed knowledge of the molecular and functional properties of the nervous system in C. elegans. Since C. elegans can be maintained in microtiter plates, it is possible to use this test system to test out 10,000 or more substances by HTS, on the living worm, in a short period of time.

The progressive sequencing of different genomes has shown that many human genes have homologs in other organisms. More than two thirds of all the human disease-associated genes known thus far have been demonstrated to be also present in the C. elegans genome. In several cases, it has been shown experimentally that these genes are functionally interchangeable. These features possessed in common demonstrate that the functions of these genes are essential for fundamental biological processes. The common features make it possible to establish these model systems for investigating human gene functions, for identifying new target genes and for developing drugs.

The present application describes, inter alia, a Parkin-encoding gene (FIG. 3; SEQ ID NO:1), which is derived from *C. elegans* and which was previously unknown, and its gene product (SEQ ID NO:2), which gene was found by analyzing *C. elegans* DNA sequences, and comparing them with the known sequence of the human Parkin gene, using bioinformatic methods.

Having knowledge of this novel gene, and concomitantly using other genes known to be connected with Parkinson's disease, such as the α-synuclein gene, it was possible to develop a nematode model which can be used to analyze neurodegenerative diseases genetically, an approach which can be used for selectively developing novel pharmaceuticals for preventing and/or treating diseases of this nature and, in particular, for preventing and/or treating Parkinson's disease and for identifying other potential diseases of this nature and, in particular, genes which elicit Parkinson's disease.

Following identification of the Parkin gene in *C. elegans*, strains of this organism in which the *C. elegans* Parkin gene was wholly or partially deleted (what are termed Parkin knock-out mutants) were isolated in the applicant's laboratory (see experimental section). These strains exhibited a phenotype which was different from that of the wild type.

This phenotype was subjected to a variety of complementation experiments. In these experiments, a part of the cosmid which contains the *C. elegans* Parkin gene and its promoter, on the one hand, and, on the other hand, the human Parkin gene, were inserted into the *C. elegans* Parkin knock-out strain in order to offset the phenotype of the inactivated *C. elegans* Parkin gene. These experiments verified, on the one hand, that the phenotype was indeed the consequence of inactivating the *C. elegans* Parkin gene and, on the other hand, that the *C. elegans* gene and the human disease-associated gene are functionally interchangeable.

Since mutations in, and deletions of, quite different regions of the Parkin gene lead to hereditary Parkinson's disease in humans, it can be assumed that expression of the disease must result from a functional loss of the Parkin gene product. We have therefore developed the *C. elegans* Parkin knock-out strains as model systems for testing pharmacologically active substances. In this connection, pharamacologically active substances are those which suppress the phenotype, i.e. it is consequently possible to identify substances which suppress the phenotype (by, for example, these substances improving the motility of the worm).

It is not always possible to use the disease-relevant gene product itself as the therapeutic target structure for the drug development. The possibility then presents itself of investigating the pertinent metabolic pathway, and the gene products involved, for their suitability as target structures in an in vivo model. The previously mentioned *C. elegans* Parkin knock-out worm strains are also outstandingly suitable for identifying new genes which are involved in the Parkin metabolic pathway. In these experiments, the knock-out worm strains are subjected to a mutagenesis and animals which no longer exhibit an altered phenotype, and which consequently move normally once again, are selected out. These animals are then subjected to genetic mapping in order to identify the gene which, having been mutated, leads to the Parkin knock-out phenotype being suppressed. This target gene may then possibly in turn be suitable for developing a drug. Aside from the model based on the Parkin gene, a transgenic nematode model in which a human α-synuclein gene is expressed in *C. elegans* under the control of specific *C. elegans* promoters was also developed. This model also reproduces important features of Parkinson's disease and can consequently also be used as a tool for developing novel medicines for treating this disease.

Expression of the human α-synuclein gene, or of derivatives of the human α-synuclein gene, in particular of mutants which induce hereditary forms of Parkinson's disease in humans, such as the α-synuclein mutant A53T, in which the amino acid alanine at position 53 is replaced with threonine, in *C. elegans* animals led, for example, to a morphological change in the head region (anterior third of the body) and/or tail region and/or in/on the vulva (posterior third of the body) of the animals, which change is characterized by a swelling (increase in the diameter of the animals) due to a functional incapacity or functional reduction in the activity of muscles and neurons. Expression of α-synuclein or its derivatives in *C. elegans* presumably modifies the function of genes, in particular those which are expressed in muscles and neurons.

Under a first aspect, therefore, the invention relates to a nemtatode which exhibits an aberrant or nonexistent expression of a gene which is connected with Parkinson's disease, in particular a Parkin gene and/or an α-synuclein gene. This nematode can be used as a model organism for neurodegenerative diseases, including those in which plaque-like deposits appear in the nervous system (amyloidoses), and, in particular, for Parkinson's disease.

In this connection, the aberrant or nonexistent expression can relate, for example, to the Parkin gene derived from *C. elegans*, to the human Parkin gene or to any homologous Parkin gene from another organism, or to an α-synuclein gene from any organism, such as a human α-synuclein gene.

In particular, the aberrant or nonexistent expression of the Parkin gene can be caused by this gene having been completely or partially deleted or by this gene having been temporarily inactivated, for example using the RNA interference (RNAi) technique which is known in the prior art.

Under another particular aspect, the nematode of the invention exhibits a phenotype which is associated with the aberrant or nonexistent expression of the Parkin gene and/or the α-synuclein gene.

The phenotype which is associated with the aberrant or nonexistent expression of the Parkin gene can, for example, be a defect in chemotaxis, a defect in egglaying, an extended period of development, a decreased number of descendants, problems in coordination, a defect in defacation, retarded locomotion or a reduced body length.

The phenotype which is associated with aberrant or nonexistent expression of the α-synuclein gene can, for example, be a defect in egglaying, a defect in the formation of the vulva, deposits of α-synuclein, an extended period of development or a decreased number of descendants.

The different phenotypes are described in further detail in the experimental section.

In addition, the invention encompasses the use of a nematode of the invention as a model organism, in particular for investigating the mechanisms involved in the development, cause and/or propagation of neurodegenerative diseases, including those in which plaque-like deposits (amyloidoses) appear in the nervous system, and, in particular, Parkinson's disease, for identifying and/or characterizing pharmaceuticals and genes for preventing or treating neurodegenerative diseases, including those in which plaque-like deposits (amyloidoses) appear in the nervous system, and, in particular, Parkinson's disease, and for identifying and/or characterizing active compounds and genes which are able to modify the effect of pharmaceuticals which are used for preventing or treating neurodegenerative diseases, including those in which plaque-like deposits (amyloidoses) appear in the nervous system, and, in particular, Parkinson's disease.

Under other aspects, the invention encompasses methods for investigating the efficacy of a substance or a gene in the treatment and/or prevention of such diseases and methods for investigating the suitability of a substance or a gene for modifying the effect of a pharmaceutical in the treatment and/or prevention of such diseases, which methods use the nematodes of the invention.

In addition, the invention also extends to the substances and genes which are identified by the methods according to the invention and which can be used for producing pharmaceuticals for preventing and/or treating such diseases and as lead substances and lead genes, respectively, for developing substances and genes, respectively, which are derived therefrom and which are active in the treatment and/or prevention of such diseases, or of substances and genes, respectively, which are suitable for modifying the effect of a pharmaceutical in the treatment and/or prevention of such diseases.

In this connection, the development of novel pharmaceuticals for treating Parkinson's disease or other neurodegenerative diseases, including those which are characterized by the deposition of protein aggregates in the nervous system and are, in particular, induced or intensified by such a deposition, can also encompass the investigation of protein-mediated interactions or the investigation of factors which are affected by these interactions.

In this connection, a pharmaceutical for treating such diseases should, in particular, be suitable for curing the disease, for alleviating individual symptoms, several symptoms or all the symptoms of the disease, or for delaying the progress of the disease.

A prophylactic treatment can be aimed at complete protection against the disease developing or simply aimed at delaying the onset of the disease.

Finally, the invention relates to an isolated nucleic acid molecule which encodes the *C. elegans* Parkin gene, to homologs and fragments of this molecule, and to a polypeptide or protein which is encoded by such a nucleic acid molecule.

DETAILED DESCRIPTION OF THE INVENTION

More specifically, the invention is based on the finding that genes of the Parkin gene family and genes of the α-synuclein gene family are biochemically or genetically connected with the development, propagation or intensification of neurodegenerative diseases, including those in which plaque-like deposits appear in the nervous system (amyloidoses), i.e. those which are induced or intensified by the deposition of protein aggregates in the nervous system, and, in particular, Parkinson's disease.

Accordingly, the invention is directed, in particular, to nematodes for use as model organisms for neurodegenerative diseases, including those in which plaque-like deposits appear in the nervous system, which nematodes exhibit an aberrant or nonexistent expression of a Parkin gene and/or an α-synuclein gene.

However, the genes which come into consideration in this regard also comprise homologous genes from other organisms. Thus, a sequence comparison based on the *C. elegans* Parkin gene showed that homologous genes were present, for example, in the following organisms:

| | |
|---|---|
| *D. melanogaster*: | Parkin (27% identical, 38% similar) |
| *H. sapiens*: | PARK2 (Parkin) (27% identical, 36% similar) |
| *M. musculus*: | Parkin (25% identical, 36% similar) |

The above genes can consequently also be introduced into the model organism.

In connection with the invention, an aberrant gene expression is understood as being, in particular, at least one of the following:
  an increased gene expression which leads to the generation of a quantity of transcription product and/or translation product of the gene concerned which is increased as compared with the wild-type gene,
  a decreased gene expression which leads to the generation of a quantity of transcription product and/or translation product of the gene concerned which is decreased as compared with the wild-type gene,
  an expression of a mutated gene, and/or
  an expression of a gene which is homologous or heterologous with respect to the organism.

In this connection, the terms "aberrant or nonexistent expression" are always to be understood in relation to an organism which is otherwise genetically equivalent, i.e. identical, but which exhibits a wild-type character with regard to this expression. The reference organism which is enlisted for the comparison can consequently be, for example, a pure wild-type organism which is found in nature, an organism from a line which has been obtained by conventional breeding methods, such as by crossing, or a transgenic organism which has already been modified by genetic mutation, i.e. with regard to genes of another type, and which, where appropriate, can additionally have been subjected to crossing. The only thing which is crucial is that the reference organism or parent organism exhibits a wild-type character with regard to the gene expression which is relevant in the present case.

The gene which is to be expressed aberrantly within the context of the invention can be a gene which is homologous or heterologous with respect to the target organism or be derived by mutation from a gene which is homologous or heterologous with respect to the target organism.

The gene which is to be expressed aberrantly can be present in the target organism
  in the complete state, i.e. together with all the appurtenant regulatory regions in addition to the coding region(s),
  together with only a part of the regulatory regions in addition to the coding region(s), or
  solely in the form of the coding regions, i.e. in combination with regulatory regions which are heterologous with respect to the gene.

In this connection, the coding regions can constitute the entirety of the coding regions of the relevant gene, or parts of these coding regions, which parts, however, at least guarantee the functionality, of the gene or the gene product, which is essential in connection with said diseases. The coding regions can also be present in the form of a fused gene, i.e. coding regions which are fused to a different protein, for example a marker protein.

Thus, within the context of the invention, the aberrant gene expression can constitute or encompass the expression of a gene which is native but heterologous with respect to the target organism.

As a rule, it will be possible to attribute increased or decreased gene expression to (a) mutation(s) in the promoter region and/or other regulatory regions, e.g. enhancer sequences, matrix/scaffold attachment regions, etc., of the relevant gene which is homologous or heterologous with respect to the target organism or to a coupling of the coding gene regions to a stronger or weaker promoter which is heterologous with respect to the coding gene region. An increased gene expression can also be brought about by the additional, and suitable, incorporation of expression-augmenting elements, such as enhancer sequences and matrix/scaffold attachment regions, into the genes which are to be expresssed aberrantly.

When a mutated gene product is expressed, one or more mutation(s) is/are present, where appropriate in addition to mutations in regulatory regions, in the coding region of the gene which is homologous or heterologous with respect to the target organism, which mutation(s) lead(s) to a change in the amino acid sequence of the translated gene product as compared with the amino acid sequence of the native gene product.

In this connection, the simultaneous presence of mutations in regions regulating gene expression and in coding regions should naturally also be included. For example, it is possible to overexpress a mutated protein in a target organism in this way.

In this connection, and depending on the individual case, the aberrant gene expression can, where appropriate, include the deletion of one or more native genes in the target organism. For example, when expressing a native or mutated heterologous gene in the target organism, it could be helpful, in individual cases, to delete the homologous gene, having the same function, in the target organism. It could be appropriate to do the same in individual cases when expressing a mutated homologous gene in a target organism.

Furthermore, preference may be given, where appropriate, to regulating the aberrant gene expression in a tissue-specific manner. For this, the genes which are to be expressed aberrantly are as a rule attached to promoter sequences which permit tissue-specific or cell-specific expression, for example in the nervous system, in particular in neurons or special neuron cell types. However, enhancer sequences which act in a tissue-specific manner are also known, which sequences are able, when suitably incorporated into a gene to be expressed, to bring about a tissue-specific increase in th e expression. Tissue-specific or cell-specific promoters and enhancers of this nature are known to specialists (see, for example, Baumeister et al., 1996; Way & Chalfie, 1989; and Hobert et al., 1997).

In addition or alternatively, it is possible, by means of coupling the relevant gene to an inducible promoter, to obtain an expression, of the relevant gene in a target organism, which can be induced by chemical stimuli or physical stimuli (e.g. temperature). In this case, it is also possible to conceive of using development-specific promoters. In both cases, it is consequently possible to specify the beginning of the expression of the relevant gene, and consequently, in particular, the appearance of phenotypes which are connected to this gene expression, at a time which can be freely selected by the user (inducible promoter) or which can be regulated by the choice of the (development-specific) promoter. In these cases, it is accordingly possible to initially allow the development of the target organism to proceed for a certain period of time unaffected by the expression of the relevant gene.

The aberrant gene expression will frequently encompass the introduction of the gene, which is to be expressed aberrantly and which is in the form of a transgene which, as explained, may be homologous or heterologous with respect to the target organism, into cells of the target organism using a construct which comprises the transgene. In the case of a transgene which is homologous with respect to the target organism, the transgene is located, after having been introduced, in a genetic environment which is different from that of the corresponding gene which is naturally present in the target organism. In this connection, the transgene can, after having been introduced into the cells, be present extrachromosomally in these cells and be expressed from this extrachromosomal construct. Alternatively, after having been introduced into the cell, the transgene is integrated into the genome of the cell and expressed as such.

A large number of standard techniques, which are, in particular, especially suited for the organism cells employed, are available to the skilled person for transforming or transfecting organism cells with constructs which contain the relevant transgenes and, more generally, for preparing the organisms according to the invention. Protocols for these standard techniques can be readily found in the literature and there will therefore be no further comments in this connection.

For example, a method for generating a nematode according to the invention which is employed as a model organism can comprise introducing an expression construct, which contains a desired transgene or a desired nucleic acid sequence, into an hermaphrodite nematode. This can be effected, for example, by means of microinjection. After descendants have hatched from the eggs of the nematode, they are allowed to develop, after which at least one descendant, which contains the desired transgene or the desired nucleic acid under the control of regulatory sequences which permit an expression which is, where appropriate, tissue-specific or cell-specific, is identified. For the purpose of this identification, the expressed construct which is used for the transfection can additionally contain a marker gene which encodes a readily detectable marker protein, where appropriate as a fusion protein.

The nematode descendant which has been identified in this way can then, if desired or necessary, be subjected, where appropriate, to a further breeding procedure, for example crossing with other nematodes which, for example, are expressing other interesting transgenes, in order to produce lines which exhibit various desired properties in addition to the aberrant or nonexistent gene expression discussed above.

If, in an organism according to the invention, it is desired to render the expression of a native gene nonexistent, several possibilities, such as a selective knock-out mutation, which is described in more detail in the experimental section, or the use of a specific antisense or sense strategy, and a selective mutagenesis, are also available for this purpose.

Another possibility of inactivating a gene is that of using the RNA interference technique, which was established in *C. elegans* about two years ago. In this technique, double-stranded RNA derived from the gene to be analyzed is introduced into the worm. This RNA is evidently cut into relatively small fragments and can subsequently become distributed throughout the animal. The RNA fragments interact, in each cell, with the corresponding messenger RNA, resulting in the transcript being broken down specifically (Zamore et al., 2000). This process leads to a loss-of-function mutation having a phenotype which, over the period of a generation, comes to very closely resemble that arising from a deletion of this gene.

There are two different possibilities for transferring the double-stranded RNA into the worm. The first-possibility is that of microinjection, with the single-stranded RNA being prepared by in vitro transcription. Sense and antisense RNA are subsequently hybridized to each other, giving rise to the double-stranded form. This is injected once into the worm and the F1 descendants of the animal are analyzed.

The second possibility is that of feeding, with the RNA being synthesized in vivo in a suitable bacterial strain. As a result of the worms growing on these feed bacteria, the RNA passes from the intestinal tract into the remaining cells, leading to the breakdown of the corresponding mRNA which has already been described above. The advantage of this approach is that the RNA is supplied continuously and the interfering effect therefore lasts longer.

In a special embodiment of the invention, more than one of the abovementioned genes is expressed aberrantly in an organism according to the invention. In addition to this, the organism can also express a Parkin gene, or a gene which is homologous to it, as a transgene and/or express an α-synuclein gene, or a gene which is homologous to it, as a transgene.

The organisms according to the invention are nematodes, in particular nematodes of the genus Caenorhabditis, for example C. elegans, C. vulgaris or C. briggsae.

All of the transgenic animals which are defined within the context of this application can be used as model organisms for neurodegenerative diseases in which, in particular, the members of the α-synuclein gene family and/or the genes of the Parkin gene family are involved, and, in particular, for selectively developing novel drugs for preventing and/or treating diseases of this nature.

In this connection, it is possible to use pharmaceutical candidate substances, in particular small molecules, to test whether the phenotype observed in the given particular case is reduced or augmented by the action of such substances. For this reason, the transgenic animals, in particular C. elegans, and, for example, those which are expressing α-synuclein, are suitable for testing novel pharmacological active compounds.

The use of nematodes has numerous advantages, particularly for identifying and characterizing pharmaceuticals and active compounds. Nematodes according to the invention exhibit, in particular, symptoms which can be observed in a quite equivalent manner in human patients who are suffering from neurodegenerative diseases, including those in which plaque-like deposits appear in the nervous system, and, in particular, those patients who are suffering from Parkinson's disease. In this connection, it is possible to readily observe or determine the symptoms in nematodes, without any great input and only a short time after the nematodes have hatched, for example only a few days after hatching. In addition to this, nematodes have short generation times, as compared to other organisms, and there is the possibility of genetically manipulating large numbers of animals and correspondingly generating large numbers of transgenic animals. There are no problems in producing relatively large numbers of identical transgenic descendants from one nematode according to the invention, which means that sufficient organisms can be provided even for the HTS of large numbers of pharmaceutical candidates or of whole substance libraries. Substance libraries of this nature can be libraries of synthetically produced substances or libraries of natural products.

When nematodes are used, mass screening of this nature can, for example, be conveniently performed in microtiter plates, with it being possible to provide one well, or, in the case of parallel samples, correspondingly more wells, available for each pharmaceutical candidate compound or active substance candidate compound.

In a method for investigating the efficacy of a substance in treating and/or preventing neurodegenerative diseases, it is accordingly possible, for example, for organisms according to the invention to be exposed to the substance and for changes which may arise in the phenotype, which is associated with the aberrant or nonexistent expression of the at least one gene connected to diseases of this nature, as has been discussed above, to be determined.

In this connection, an attenuation of the observed phenotype, an abolition of the observed phenotype or a retardation in the deterioration of the observed phenotype with time which is otherwise observed in the absence of the pharmaceutical treatment, indicates that the investigated substance is effective as a pharmaceutical in the treatment and/or prevention of such diseases. A deterioration in the observed phenotype over and above the extent observed in the absence of pharmaceutical treatment, or an acceleration of the deterioration which is normally observed in the absence of pharmaceutical treatment, indicates that the investigated substance is contraindicated in connection with these diseases.

In order to confirm the results which have been obtained, it will always be appropriate to observe control organisms which are not exposed to the substance to be investigated. Since, as a rule, a deterioration in the phenotype, i.e. in the symptoms which are observed in connection with the aberrant or nonexistent expression of the at least one gene connected with diseases of this nature, will be observed over time in the target organisms, it will as a rule be necessary, in comparative investigations (comparative investigations using different pharmaceutical candidate substances or comparative investigations with and without a pharmaceutical candidate substance), to use organisms which are equivalent to each other and which are of the same age, for example nematodes of the same line which have hatched at the same point in time.

In a method for investigating the suitability of a substance for modifying the effect of a pharmaceutical in the treatment and/or prevention of neurodegenerative diseases, including those in which plaque-like deposits appear in the nervous system, it may, for example, be necessary to perform the following steps:

to expose an organism according to the invention to the pharmaceutical and to determine the changes, which arise as a result of the effect of the pharmaceutical, in the phenotype which is associated with the aberrant or nonexistent expression of the at least one gene connected to such diseases, as have been discussed above, to expose at least one further specimen of the organism of the type used in the preceding step to the pharmaceutical in the presence of the substance and to compare any changes which may arise in the phenotype with the changes, which arise due to the effect of the pharmaceutical on its own, in the phenotype which is associated with the aberrant or nonexistent expression of the at least one gene connected to such diseases, as have been discussed above.

The substance to be investigated can be added before, at the same time as, or after the addition of the pharmaceutical, which is in each case employed, to the assay system containing the organism according to the invention. It is also possible for the substance and the pharmaceutical to be previously incubated together before being added to the assay system.

In this connection, an attenuation of the observed phenotype which is augmented in the presence of the substance, an abolition of the observed phenotype which newly occurs in the presence of the substance, or a chronological retardation, which is stronger in the presence of the substance, of the changes in the observed phenotype which are otherwise observed in the presence of the pharmaceutical without any addition of the substance, indicates that the investigated substance is active as an effect-modifying agent which augments the effect of the pharmaceutical, used in the assay, in the treatment and/or prevention of such diseases (=agonistic effect). A deterioration, which is observed in the presence of the substance, of the observed phenotype as compared with the phenotype which is observed in the presence of the pharmaceutical on its own, a complete abolition of the effect of the pharmaceutical, or a more minor retardation of the deterioration which is normally observed despite the presence of the pharmaceutical, show that the investigated substance is contraindicated (=antagonistic effect) in such diseases.

That which has been said in the preceding paragraphs also applies, in a corresponding manner, with regard to the reference organisms which are to be employed for comparative purposes, including organisms which are not treated with pharmaceutical and substance and organisms which are only treated with the substance, i.e. which are not treated with the pharmaceutical.

The identification or characterization of pharmaceuticals and modifying substances which is effected using the organisms and methods according to the invention can also be effected using substance mixtures, e.g. natural product extracts or fermentation broths, with the substance mixture initially being tested and, when activity has been demonstrated, the mixture then being separated or fractionated into individual substances, where appropriate stepwise, in the direction of continually increasing purity, in order to finally arrive at the pure active compound or the pure modifying substance. Accordingly, during the course of the separation or fractionation, the method according to the invention will as a rule be repeated as often as required for identifying the fraction which in each case contains the active compound or the modifying substance.

The definitions of the methods according to the invention which are presented should consequently also encompass substances which are present in the form of a mixture with other compounds.

The invention also extends to substances which are effective in the treatment and/or prevention of neurodegenerative diseases, including those in which plaque-like deposits appear in the nervous system, and substances which are suitable for modifying the effect of a pharmaceutical in the treatment and/or prevention of such diseases, which substances have been identified using one of the methods according to the invention which have just been explained. It is possible to use these substances to produce a variety of pharmaceuticals.

The invention also extends to the use of a substance according to the invention as a lead substance for developing substances which are derived from it and which are effective in the treatment and/or prevention of neurodegenerative diseases, including those in which plaque-like deposits appear in the nervous system, or substances which are suitable for modifying the effect of a pharmaceutical in the treatment and/or prevention of such diseases.

Proceeding from an appropriate lead substance, the derived substances can be obtained by means of one or more of the methods of chemical derivatization which the skilled person customarily employs in this connection. Only by way of example, a salt formation, an esterification, an etherification or an amide formation may be mentioned in the case of a lead substance being present in the form of an organic acid, or the formation of a salt with an organic or inorganic acid may be mentioned in the case of a lead substance which is present in the form of an amine. Hydroxyl groups which are present on the lead substance can be used, for example, for etherification or customary reactions of a different nature. The invention also encompasses any types of formation of addition compounds and solvates and of substitutions which can be performed on the backbone chain of a lead substance, for example on an aromatic ring structure which is present in this chain. Substitutions of hydrogen atoms, halogen atoms, hydroxyl groups, amine groups, carboxylic acid groups or alkyl groups, or substitutions by such groups or atoms, can, for example, be performed.

Under another aspect, the invention furthermore relates to the use of the organisms, according to the invention, for identifying and/or characterizing other genes which are connected with the mechanisms involved in the genesis, the course and/or the propagation of neurodegenerative diseases, including those in which plaque-like deposits appear in the nervous system, in particular Parkinson's disease;

for identifying and/or characterizing genes which, in the mutated or unmutated state, are active in the prevention or treatment of neurodegenerative diseases, including those in which plaque-like deposits appear in the nervous system, in particular Parkinson's disease, and for identifying and/or characterizing genes which, in the mutated or unmutated state, are able to modify the effect of pharmaceuticals and/or genes which are employed for the prevention or treatment of neurodegenerative diseases, including those in which plaque-like deposits appear in the nervous system, in particular Parkinson's disease.

In analogy with the search for pharmaceuticals which suppress or augment a particular phenotype which is associated with neurodegenerative diseases, such as Parkinson's disease, the nematodes according to the invention, e.g. *C. elegans*, can also be used for identifying other genes which have the same function. A transgenic strain according to the invention, or a strain which is mutant in one of the candidate genes exemplified above, is used for this purpose. In a following step, the phenotype which is induced by the transgene or the mutation is manipulated by means of (a) additional mutation(s) in (an) other gene(s). This is effected, as a rule, by means of undirected mutagenesis, for example by means of using mutagenizing chemicals (e.g. MMS, methyl methanesulfonate; EMS, ethyl methanesulfonate; NNG, N-methyl-N'-nitro-N-nitrosoguanidine) or irradiation.

In this way, it is possible to find additional mutations which offset or amplify the phenotype (suppressor or enhancer mutants). The genes which are affected are candidates for other genes in the same signal pathway or candidates for genes in parallel signal pathways. Each of these genes which have been newly found in this way therefore constitutes another target gene for a pharmacological intervention, for example for identifying or developing pharmaceuticals (for example possessing activity toward a product of the gene in question) or for developing genetic therapeutic agents.

Alongside the pharmacological aspect, this aspect constitutes one of the most important aspects of the animal models according to the invention and, in particular, of the *C. elegans* animal model (headword: "pathway dissection", identification of the genetic components of a signal pathway).

Accordingly, the invention also encompasses a method for identifying and/or characterizing genes which, in the mutated or unmutated state, are active in the prevention or treatment of neurodegenerative diseases, including those in which plaque-like deposits appear in the nervous system, in particular Parkinson's disease, which method comprises the following steps, performing an undirected mutagenesis on organisms according to the invention, determining any changes in the phenotype, which is associated with the aberrant or nonexistent expression of the at least one gene connected with such diseases, as have been exemplified above, which it may be possible to observe in the organisms resulting from the mutagenesis, as compared with the starting organisms which were used for the undirected mutagenesis, and identifying the gene(s) which, as a consequence of its (their) mutation, is/are responsible for the changes in the phenotype which were observed in the preceding step.

The invention also relates to a method for identifying and/or characterizing genes which are able, in the mutated or unmutated state, to modify the effect of pharmaceuticals and/or genes which are used for the prevention or treatment of neurodegenerative diseases, including those in which plaque-like deposits appear in the nervous system, in particular Parkinson's disease, which method comprises the steps of:

performing an undirected mutagenesis on organisms according to the invention, generating descendants of identical type from the organisms resulting from the mutagenesis, determining, in the descendants which are in each case identical, a phenotype which may possibly be present and which is associated with the aberrant or nonexistent expression of the at least one gene connected to such diseases, as have been exemplified above, comparing the phenotype which was determined in the descendants in the preceding step with the corresponding phenotype of the starting organisms according to the invention, determining, in the descendants which are in each case identical and which exhibit the same phenotype as the starting organisms, changes in the phenotype, which are associated with the aberrant or nonexistent expression of the at least one gene connected to such diseases, as have been exemplified above, in the presence of the pharmaceutical to be investigated or when the gene to be investigated is expressed, and comparing the changes which have been determined in the phenotype with the changes in the phenotype of the starting organisms in the presence of the pharmaceutical to be investigated or when the gene to be investigated is expressed, in order to ascertain any differences in the phenotype change which may possibly be occurring, and identifying the gene(s) which, as a consequence of its (their) mutation, is/are responsible for the differences in the phenotype changes which may possibly have been observed in the preceding step.

The genes in question can be identified in a variety of ways known to skilled persons in this field, for example by means of recombination analysis. If the sought-after gene can be restricted to a limited number of candidate genes, it is also possible, for example, to carry out a directed mutation of corresponding starting organisms and to determine the phenotype changes or differences in phenotype change resulting therefrom in order to ascertain whether, after mutation, a candidate gene does in fact come into consideration for the phenotype changes or differences in phenotype change.

In this connection, it is also possible, for example, for one of the following methods to be used:

(a) a method for investigating the activity of a gene in the treatment and/or prevention of neurodegenerative diseases, including those in which plaque-like deposits appear in the nervous system, which method comprises expressing the mutated or unmutated gene in an organism according to the invention and determining changes in the phenotype which is associated with the aberrant or nonexistent expression of the at least one gene connected with such diseases, as has been exemplified above, or (b) a method for investigating the suitability of a gene for modifying the effect of a pharmaceutical in the treatment and/or prevention of neurodegenerative diseases, including those in which plaque-like deposits appear in the nervous system, with the method comprising, exposing an organism according to the invention to the pharmaceutical and determining the changes which occur, due to the effect of the pharmaceutical, in the phenotype which is associated with the aberrant or nonexistent expression of the at least one gene connected to such diseases, as have been exemplified above, exposing at least one further specimen of the organism of the type used in the preceding step, in which organism the gene to be investigated is additionally expressed, to the pharmaceutical, and comparing any changes which may possibly occur in the phenotype, which is associated with the aberrant or nonexistent expression of the at least one gene connected to such diseases, as have been exemplified above, with the changes in the phenotype which occur due to the effect of the pharmaceutical on its own.

For the purpose of identifying pharmaceuticals and active substances, it is possible to use the newly identified genes to generate corresponding organisms which exhibit aberrant or nonexistent expression with regard to those newly identified genes and to investigate pharmaceutical candidates entirely in accordance with the above exemplifications. Everything which has previously been stated, for example with regard to organisms according to the invention, with regard to identifying or investigating pharmaceuticals, with regard to producing pharmaceuticals, etc., applies here in a corresponding manner.

Finally the invention also encompasses the use of the specific, *C. elegans*-derived Parkin gene for producing a gene therapeutic agent for preventing' or treating neurodegenerative diseases, including those in which plaque-like deposits appear in the nervous system (amyloidoses), and, in particular, Parkinson's disease. Such gene therapeutic agents are used, in particular, when defects or mutations have been identified in a particular one of said genes in a patient or an individual who is not yet exhibiting any symptoms of such a disease and these defects or mutations are known to be connected with the onset, the course or the severity of such diseases and possibly also the transmission of such diseases to descendants.

In addition to this, other aspects of the invention relate to isolated nucleic acid molecules, in particular DNA molecules, but also RNA molecules, for example, which encode a *C. elegans* Parkin having the amino acid sequence given in FIG. 3, in particular those molecules which exhibit a nucleic acid sequence given in FIG. 3. The invention also encompasses isolated nucleic acid molecules whose nucleotide sequence exhibits at least 75%, in particular at least 80%, especially at least 85%, preferably at least 90%, particularly preferably at least 95%, and most preferably at least 98%, sequence similarity to the abovementioned nucleic acid molecules, in particular those which hybridize with the abovementioned nucleic acid molecules under stringent conditions. Preferably, such a hybridization takes place under low stringency conditions while, in another embodiment, it also takes place under high stringency conditions. Within the context of this description, low stringency conditions are understood as meaning a hybridization in 3×SSC at from room temperature to 65° C. and high stringency conditions are understood as meaning a hybridization in 0.1×SSC at 68° C. SSC is the abbreviation for a 0.15 M sodium chloride, 0.015 M trisodium citrate buffer.

The nucleic acid molecules according to the invention which exhibit nucleic acid sequence similarity with the nucleic acid sequence given in FIG. 3 include, in particular, all the allelic variants of the given nucleic acid sequence.

The invention also extends to the nucleic acid molecules which in each case have a nucleic acid sequence which is complementary to the above-exemplified nucleic acid sequences.

In the present connection, the term "isolated nucleic acid molecule" relates to nucleic acid molecules which are present in a form in which they are essentially purified from the main quantity of the nucleic acid molecules of a different nature derived from the parent cells and/or producer cells. However, preparations of isolated nucleic acid molecules according to the invention can perfectly well contain other constituents, such as salts, medium substances or residual constituents of the producer cells, such as various proteins.

The invention also extends to fragments of the above-exemplified nucleic acid molecules, in particular those which contain nucleic acid segments which encode amino acid sequence regions which are necessary for the function of the expression product, i.e. Parkin. In the latter case, the expression product of such a nucleic acid fragment can exhibit an efficacy/activity which is equivalent to the complete Parkin protein or else an efficacy/activity which is increased or decreased; in every case, preference is given to the expression product still being able, to some degree, to exert the effect(s) exerted by the complete Parkin protein. In addition, the invention also extends to those fragments which can be used, for example, as highly specific hybridization probes, PCR primers or sequencing primers, or else as "antisense" or "sense" nucleotides for the specific "homology-dependent gene silencing" of the Parkin gene. Depending on their purpose, such fragments will encompass at least 15 nucleotides, but frequently 25 or more nucleotides. For such purposes, a nucleic acid fragment according to the invention can also, if necessary, possess one or more labeling or detection molecule(s), for example a digoxigenin molecule or a biotin molecule.

The invention furthermore encompassses constructs, vectors, plasmids, cosmids, bacmids, YACs, BACs, viral genomes or phage genomes which contain one of the exemplified isolated nucleic acid molecules. In the present case, constructs are understood as being, inter alia:
- constructs which contain the nucleic acid molecules or nucleic acid molecule fragments according to the invention under control of a promoter,
- gene constructs which contain the nucleic acid molecules or nucleic acid molecule fragments according to the invention fused to genes or gene segments of another type,
- constructs which, for example for a use as PCR primers, comprise nucleic acid fragments according to the invention which have been supplemented with additional nucleotide sequence segments which provide suitable restriction sites for a cloning (of the products resulting from the PCR amplification).

Another aspect relates to the polypeptides or proteins which are encoded by the exemplified nucleic acid molecules, in particular to a C. elegans Parkin having the amino acid sequence given in FIG. 3 and to polypeptides or proteins which are derived therefrom by the substitution, modification, deletion, insertion or addition of amino acids and which exhibit at least 75%, in particular at least 80%, especially at least 85%, preferably at least 90%, particularly preferably at least 95%, and most preferably at least 98%, sequence similarity with the abovementioned amino acid sequences. The invention also encompasses fragments of the polypeptides or proteins which are explicitly specified above and, in particular, those which contain amino acid sequence segments which are essential for the function of the C. elegans Parkin protein. In a preferred embodiment of the invention, these fragments are still able, to some degree, to exert the effect(s) exerted by the complete Parkin protein. The invention also encompasses fusion proteins which contain the polypeptides, proteins or protein fragments according to the invention fused to a protein of a different type or to a protein segment of a different type, for example a marker protein or indicator protein.

The invention also extends to transgenic organisms, in particular microorganisms, e.g. bacteria, viruses, protozoa, fungi and yeasts, algae, plants or animals, and also parts, e.g. cells, and propagation material, e.g. seeds, of such transgenic organisms, which comprise a recombinant nucleic acid sequence, where appropriate integrated into a chromosome or else extrachromosomally, which sequence contains a nucleic acid molecule according to the invention, as has just been exemplified, as a transgene.

Under a preferred aspect, the transgenic organisms will also express the polypeptide or protein, i.e. C. elegans Parkin or a polypeptide or protein derived therefrom, which is encoded by the abovementioned transgene.

Particularly interesting uses of the C. elegans Parkin gene, or of mutants thereof, have already been exemplified in earlier sections of this description.

BRIEF EXPLANATION OF THE FIGURES

FIG. 3: Amino acid sequence and cDNA nucleic acid sequence of the C. elegans Parkin coding region (SEQ ID NO:1 and 2); differences in the nucleic acid sequence as compared with the sequence available on the Internet (CAB04599.1, determination nonexperimental) are identified by capital letters; determination by RNA isolation, cDNA preparation and subsequent sequencing.

FIG. 4 : (a) Pattern of expression of GFP under the control of the C. elegans Parkin promoter and (b) pattern of expression of the C. elegans Parkin-GFP fusion construct (see pLG0126 in FIG. 2) under the control of 653 bp of the C. elegans Parkin promoter in C. elegans (cf. experimental section 2.). Parkin-GFP is expressed in most neurons.

FIG. 12: Phenotype of transgenic worms which are expressing human α-synuclein A30P which was integrated into the genome and under the control of the sel-12 promoter. (A) Nomarski micrograph of a worm whose vulva is protruding from the body (B; C) transgenic worm with protruding vulva and disrupted egglaying, containing juveniles which have already hatched.

EXPERIMENTAL SECTION

1. Bioinformation

The *C. elegans* homolog of the human Parkin gene was found by using the BLAST program to search the *C. elegans* sequences which are made available by the National Center for Biotechnological Information Nested PCR primer pairs for identifying deletions were designed using the Primer3 program from MIT in Cambridge and a window of 3.2-3.3 kb, and synthesized.

2. Pattern of Expression of Parkin in *C. elegans*

The expression of the Parkin gene in *C. elegans* was analyzed using GFP reporter genes (GFP=greeen fluorescent protein).

I. In a first step, the plasmid pBY1013, which contained 4085 bp of the Parkin promoter and the GFP gene, was constructed.

4085 bp from the 5' region of the Parkin locus, amplified as a PCR product using the primers

```
                                                    (SEQ ID NO:5)
RB850    GGGCCGCGGCATGCGAATACAATGACGTAAGCGACGTGG, (SEQ ID NO:6)
RB851    CCCGTCGACTCATCAGACATGCTTCATGAGAGC
``` were cloned, as an SphI/SalI PCR fragment, into the vector pPD95.75 (Dr. Andre Fire, Carnegie Institution of Washington, Baltimore, Md., USA).

A PCR product obtained from an amplification using the primers

```
RB853
                                                    (SEQ ID NO:7)
GGGCCGCGGTTCGAATTTGAAGCTCGCTGCGT

Figure 4B:
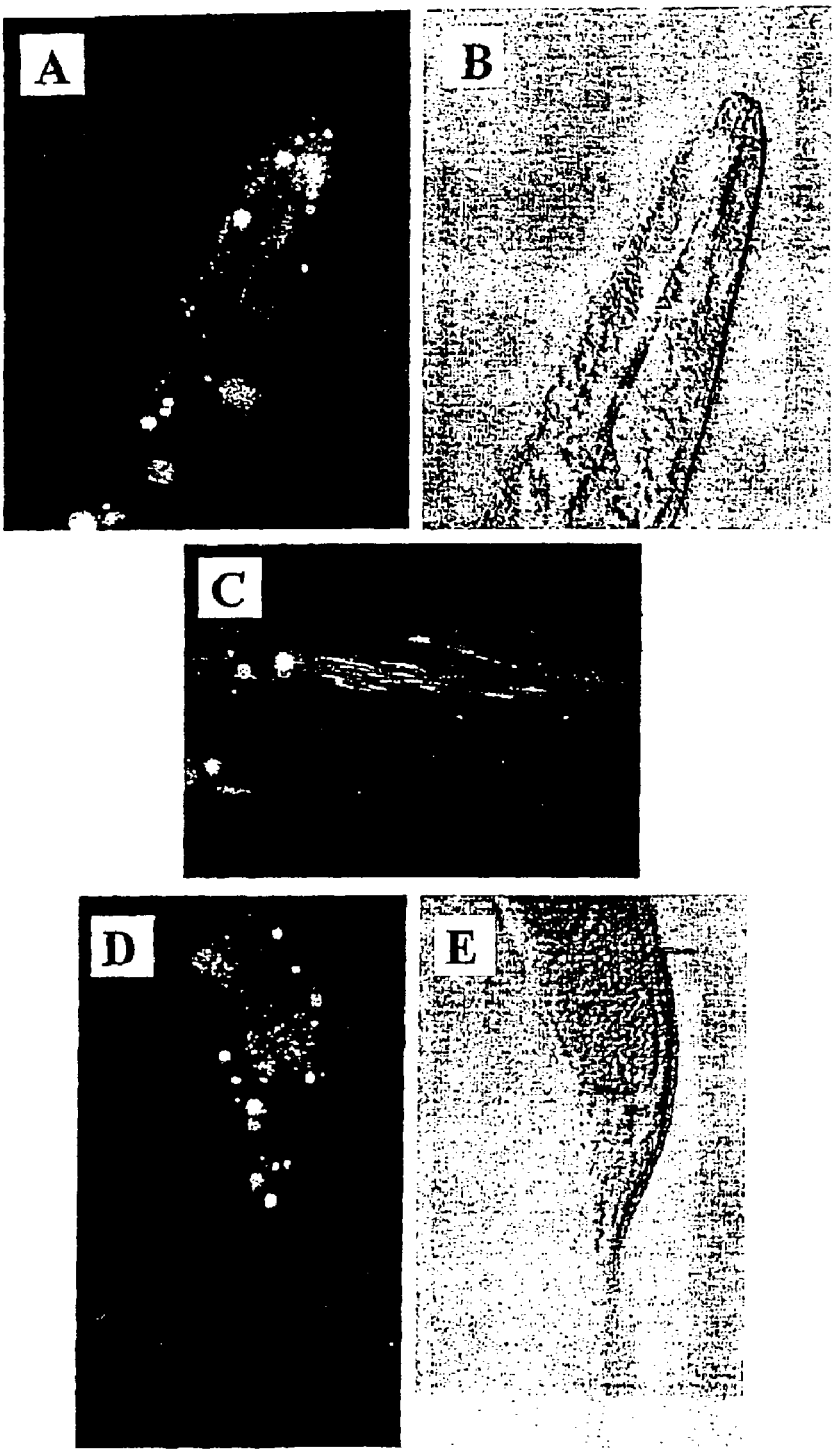
FIG. 4b shows neurons in the head region (A) and tail region (D) together with the appurtenant Nomarski micrographs (B and E). Parkin-GFP is also expressed in most muscles. (C) in FIG. 4b shows muscle fibers in the middle of the worm.

RB916
                                                    (SEQ ID NO:8)
CGCCCGGGAGCTCGTCGACCTATTAAACCAATGGTCCCATTGACACTC
``` was cloned, as an NheI/SalI fragment, into the GFP vector pBY1023. *C. elegans* wild-type animals were transformed with the resulting plasmid pBY1013. Semistable transgenic lines were isolated. These exhibited GFP expression in a large number of neurons and muscles (see FIG. 4a).

Particular emphasis is to be given to the expression in
the anal-sphincter and anal-depressor muscles for controlling defacation,
the vulva and uterus muscles for controlling egglaying
in the entire pharynx (muscles and neurons),
tail neurons, in particular those with a long process in the ventral nerve cord,
head neurons in the region outside of the pharynx.

II. Preparing the plasmid pLG0126 (contains 653 bp Parkin promoter+Parkin gene+GFP gene as a fusion construct)

Figure 2:
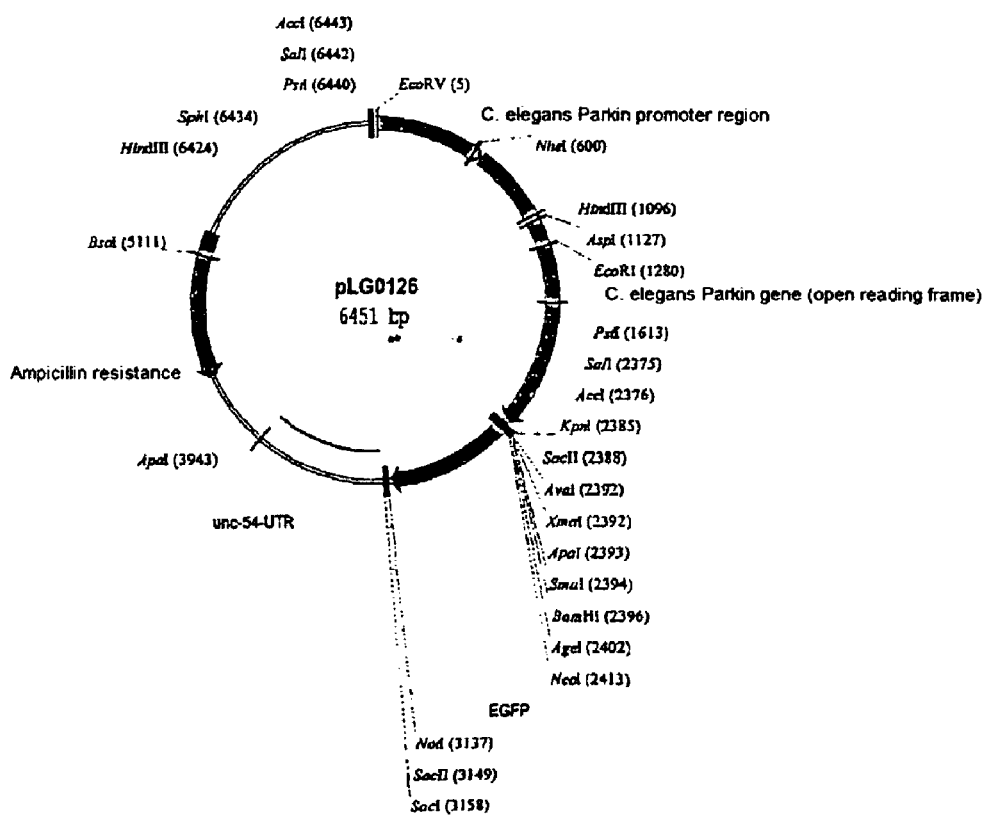
FIG. 2: Plasmid pLG0126, which contains the C. elegans Parkin promoter and the C. elegans Parkin-GFP fusion construct (SEQ ID NO:3) (promoter: 2-654; Parkin gene: 655-2371; exon 1: 655-723; exon 2: 769-914; exon 3: 1005-1437; exon 4: 1484-1574; exon 5: 1854-2058; exon 6: 2112-2186; exon 7: 2233-2371; GFP: 2414-3133; 3'-UTR of unc-54: 3179-3923; and ampicillin resistance gene: 5249-4389).

3432 bp from the 5' promoter region of the Parkin gene were excised from pBY1013 by means of inverse PCR and filled in once again using Klenow polymerase. The 1717 bp Parkin gene was then cloned into the resulting plasmid downstream of the Parkin promoter and upstream of the GFP (in the same reading frame as the Parkin gene). The resulting plasmid pLG0126 (FIG. 2) was transformed into *C. elegans* wild-type animals. Semistable transgenic lines were isolated. As in the case of plasmid pBY1013, these lines exhibited GFP expression in a large number of neurons (e.g. head, tail and pharynx) and muscles (e.g. pharynx, vulva and uterus) (see FIG. 4b).

3. Preparing *C. elegans* Eggs

Approx. 8,000 young adult wild-type animals were rinsed with M9 buffer (22 mM $KH_2PO_4$, 42 mM $Na_2HPO_4$, 86 mM NaCl, 1 mM $MgSO_4$) from the agar plates and collected in 15 ml Falcon tubes until all the worms had been detached. After that, the worms were centrifuged for 5 min-and the supernatant was aspirated off. The worm pellet was taken up in 10 ml of M9 buffer and centrifuged once again at 3000 rpm for 3 min. After the latter procedure had been repeated, 10 ml of bleach solution (1.44% NaClO, 0.25 M KOH) were added to the worm pellet. After shaking for 4 min, the egg preparation was centrifuged at 1,500 rpm for 30 s and the supernatant was aspirated off and the egg pellet taken up in 10 ml of M9 buffer. After that, the pellet was washed 5 times with in each case 10 ml of M9 buffer and in each case centrifuged at 3,000 rpm for 1-2 min.

4. Preparing Mutagenized Nematode Worms

In order to prepare the mutagenized nematode worm strains, the egg pellet which resulted from the egg preparation was taken up in 10 ml of M9 buffer and shaken in an overhead shaker at 20° C. for 20 h. On the following day, the hatched L1 larvae (in each case 6,000 per plate) were sown on 8 plates (OP50 bacteria-inoculated agar plates of 9 cm diameter) and incubated at 15° C. for 60-70 h. After the animals had been rinsed off with M9 buffer and collected in Falcon tubes, they were washed in M9 buffer until the supernatant was no longer opacified by bacteria (centrifugations were in each case at 1,000 rpm for 3 min). Subsequently, 10,000-15,000 animals were transferred into a new Falcon tube and treated with trimethylpsoralen (30 μg/ml). The mixture was incubated for 15 min on the overhead shaker in the dark and, after the worms had settled after 3 min, they were added dropwise to a dry agar plate. After the worms had been allowed to dry for 2-5 min, they were irradiated for 1 min at 365 nm with a dose of 540 μW/cm$^2$. After that, the worms were rinsed off with M9 buffer and centrifuged down and the pellet was added to 3 new plates (9 cm in diameter and inoculated with OP50 bacteria). After the plates had been incubated at 20° C. for 24 h in the dark, an egg preparation was carried out (see above) and incubated overnight at 20° C. After that the synchronized and mutagenized F1/L1 animals were centrifuged down and taken up in S complete medium (200 mM NaCl, 50 mM KH$_2$PO$_4$, 13 mM cholesterol, 10 mM sodium citrate, 3 mM CaCl$_2$, 3 mM MgSO$_4$, 100 U of nystatin/l, 100-fold PSN antibiotic mix, trace elements, HB101 bacteria having an OD$_{600\,nm}$ of 2.0) (400 worms/ml). The worm suspension was sown in 17-33 microtiter plates at the rate of 50 μl per well and the plates were incubated at 20° C. for 5-6 days. After in each case one quarter (12.5 μl per well) of the worm suspension had been removed for preparing the genomic DNA and the well lysates, the worm plates were placed in storage boxes for long-term storage, sealed with parafilm and incubated at 15° C.

5. Preparing Pooled Genomic DNA

In each case one quarter of the worm suspension (12.5 μl per well) from all the 96 wells from an original plate were combined in a 15 ml Falcon tube and 1 ml of M9 buffer was added. The Falcon tubes were washed twice with in each case 10 ml of M9 buffer (centrifugation at 3,000 rpm for 3 min), after which 4 ml of washing buffer (20 mM tris buffer, pH 7.5, containing 100 mM NaCl and 50 mM EDTA) were added. After a centrifugation at 3,000 rpm for 3 min, all but 1 ml of the supernatant was aspirated off and the remaining supernatant, together with the pellet, was transferred to an Eppendorf tube using a Pasteur pipette. The mixture was centrifuged at 14,000 rpm for 1 min in an Eppendorf centrifuge and all but 250 μl of supernatant was taken off. 350 μl of washing buffer were added to this remaining 250 μl and the whole was frozen at −80° C. After rethawing, 10 μl of 10% SDS, 2 μl of proteinase K (20 mg/ml) and 1 μl of β-mercaptoethanol were added, after which the whole was mixed by tipping and then digested at 65° C. for 1 h. Once again, 2.5 μl of proteinase K (20 mg/ml) were added and the mixture was incubated for 1 h. After that, 2.4 μl of RNAse A (10 mg/ml) were added, and the whole was mixed by tipping and then incubated at 37° C. for 15 min. After 250 μl of protein precipitation solution (Promega) had been added, each Eppendorf tube was vortexed for 10 s, placed on ice for 5 min and centrifuged (at 14,000 rpm for 10-15 min, if possible while being cooled). The supernatant, which contained the DNA, was carefully taken off and added to a new Eppendorf tube. 500 μl of isopropanol were added to these supernatants, after which mixing was carried out by tipping and the tubes were then placed on ice for 5 min and subsequently centrifuged at 14,000 rpm for 10-15 min. The supernatant was taken off and discarded. 500 μl of 70% ethanol were added to the pellet, which contained the DNA, after which the tubes were mixed by tipping and centrifuged at 14,000 rpm for 10 min. The supernatant was very carefully pipetted off. The remainder of the ethanol was evaporated off by placing the open Eppendorf tubes in a heating block at 37° C. The pellet which remained was taken up in 350 μl of 10 mM tris, 1 mM EDTA and left to stand at room temperature overnight. On the following day, the genomic DNA was placed in a heating block at 50° C. for 1 h and distributed on PCR plates.

6. Preparing Well Lysates

Well lysates were prepared from a quarter of the sown-out worm suspension (12.5 μl) by 12.5 μl of the worm suspension being taken up in 12.5 μl of lysis buffer (20 mM tris buffer, pH 8.2, containing 100 mM KCl, 5 mM MgCl$_2$, 0.9% NP-40, 0.9% Tween-20, 0.02% gelatin, 14.4 μg/ml of proteinase K), being digested at 65° C. for 6 h, then being incubated at 95° C. for 15 min in order to inactivate the protein kinase K, and then being frozen down at −80° C. after having been cooled briefly.

7. Using Nested PCR to Identify Deletions

Nested PCR was used to test genomic DNA plate pools and well lysates for deletions. In nested PCR, a PCR is first of all carried out using two external primers and a PCR is then carried out on the resulting product using two internal primers, in order to obtain higher specificity and better amplification. The genomic DNA was stamped directly, using a sample stamper (V & P Scientific, San Diego, USA), into a mixture (reaction volume of 25 μl) which contained Taq polymerase (Hoffmann-La Roche, 0.5 units/reaction), dNTP mixture (0.2 mM) and primers (0.4 μM). The reaction ran for 35 cycles at 92° C. for 20 sec, 56° C. for 1 min and 72° C. for variable times (15-120 s) in Perkin-Elmer machines of the 9700 type.

8. Analyzing the Deletions

PCR products were analyzed using agarose gels (1% agarose), and sequenced when identifying desired deletions.

9. Isolating the Mutants

Figure 1:
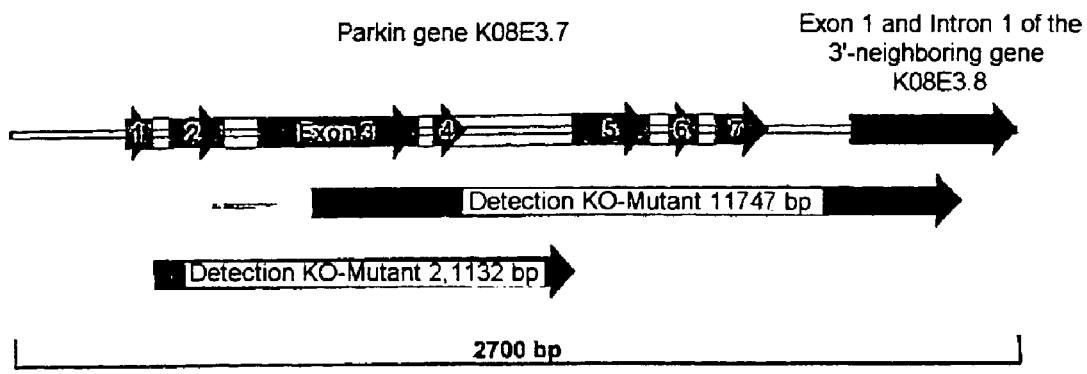
FIG. 1: Diagram of the structure of the C. elegans Parkin gene together with exons and introns and the location of the deletions in the two KO mutants KO1 and KO2 (location: Parkin gene: 308-2027; KO1 deletion: 804-2550 and KO2 deletion: 382-1513).

The worms present in the well which was identified as containing worms having the deletion in the target gene, i.e. having shorter PCR products than in the case of the wild-type worms, were taken out of the liquid culture and added individually to agar plates. After having self-replicated successfully, the parent animals were analyzed for homozygous and heterozygous worms using various primers which lay within and outside the deletion. Positive strains, i.e. worm strains having deletions in the target gene in either one (heterozygous) or both (homozygous) alleles were outbred five times with wild-type worms in order to eliminate other potential mutations. Homozygous strains which were outbred four times were used for the subsequent experiments. The mutants depicted in FIG. 1, i.e. Parkin KO1 (strain designation XY1003) and Parkin KO2 (strain designation XY1046), were obtained in this connection.

10. Phenotypinq the Parkin knock-out mutants KO1 and KO2
  a) Chemotaxiassay

Figure 6:
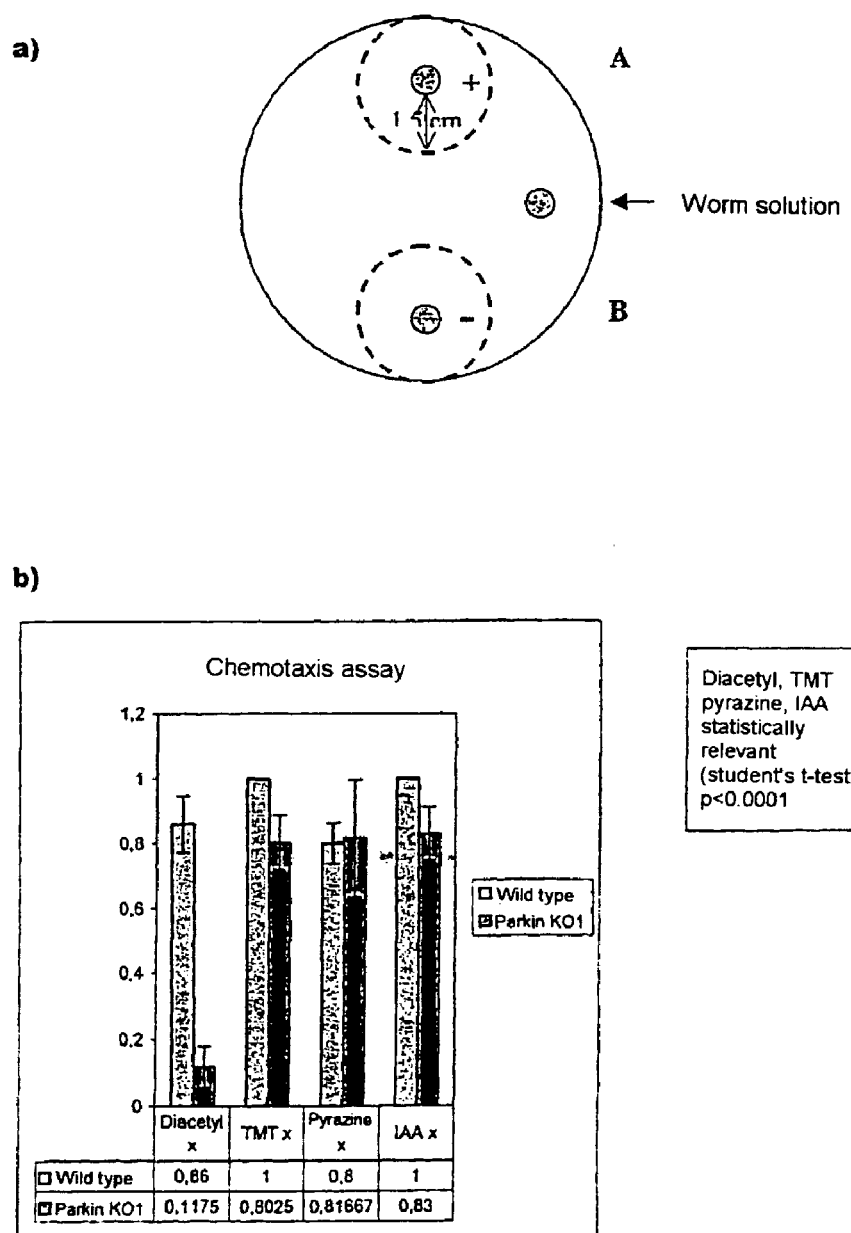
FIG. 6: a) Pattern of loading onto the plate in the chemotaxis assay; b) results of the chemotaxis assay in the case of the *C. elegans* Parkin KO1 worms.

Method:

Four plates composed of 1.6% agar, 5 mM KH$_2$PO$_4$, 1 mM CaCl$_2$ and 1 mM MgSO$_4$ were used per worm strain to be tested. The plates were divided up as shown in FIG. 6*a*).

1 μl of NaN$_3$ (1 M) was in each case applied at (+) and (−). Subsequently, 1 μl of the previously diluted attractant was applied at (+) while 1 μl of EtOH (100%) was applied at (−). The worms were cultured with *E. coli* on eight large agar plates, then washed off with H$_2$O and Tween, washed 1×at 1000 rpm and taken up in 1 ml of H$_2$O and Tween. 10 μl of the worm suspension (approx. 100 worms) were applied to each test plate. By holding the test plate vertically, the worms were distributed over a line which resulted in identical distances to the attractant and a negative control being achieved.

The attractants used were isoamyl alcohol (1:200), diacetyl (1:1000), pyrazine (10 mg/ml) and 2,4,5-trimethylthiazole (1:1000). All the substances were diluted in 100% EtOH. The assay was carried out at room temperature for 90 min. After that, chloroform was added to the lids of the test plates in order to immobilize the worms.

Evaluation:

The worms which were present within a radius of 1.5 cm around the attractant (A) or round the negative control (B) after the time had expired were counted. The chemotaxis index was calculated from these values as follows:

$$\frac{A-B}{A+B}$$

Results:

The result is shown in FIG. 6*b*).

The Parkin KO1 worm strain did not react to the attractant diacetyl (odr).

The Parkin KO2 worm strain behaved in a similar manner (results not shown).

b) Period of Development

Method:

10 eggs of the worm strain to be tested were in each case tipped onto a small plate. The time which elapsed until the first eggs were once again lying on the plate was determined.

Figure 7:
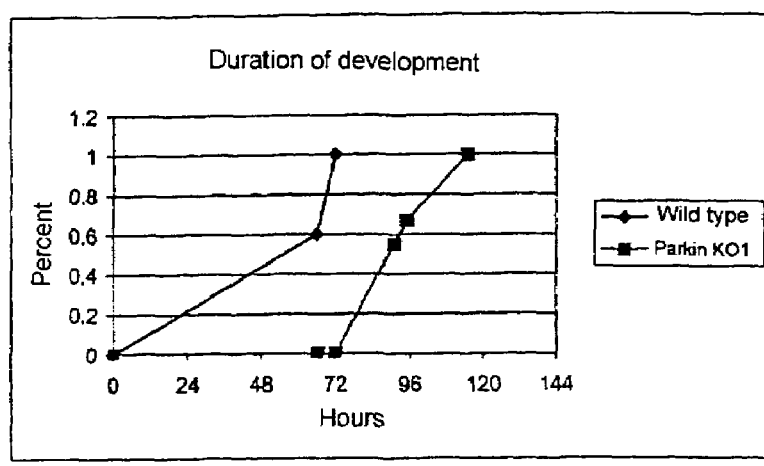
FIG. 7: Duration of the development of the *C. elegans* wilde-type worms and the Parkin KO1 worms.

Results:

In the case of the wild-type, 100% of the worms had laid their first eggs once again after 72 hours. In the case of the Parkin KO1 worm strain, the first eggs had only been laid after more than 100 hours. The Parkin KO1 development period was therefore retarded, as shown in FIG. 7.

c) Analysis of Freshly Laid Eggs

Figure 8:
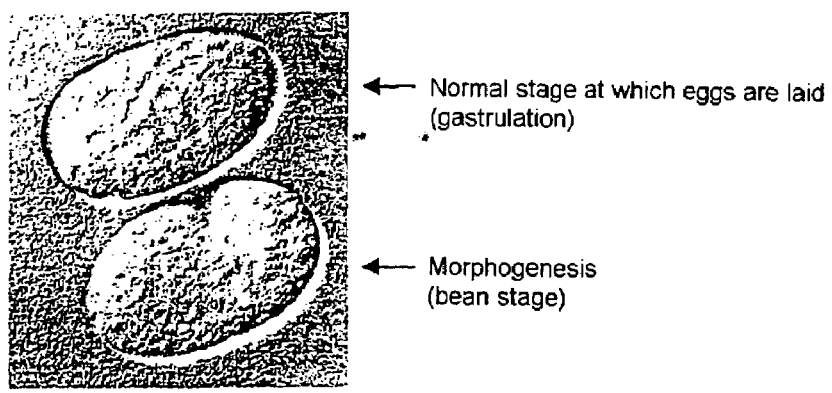
FIG. 8: Micrograph of eggs which were laid by Parkin KO2 worms.

Method:

Three adult worms were transferred to a fresh plate. After from 30 to 60 min, it was possible to use Nomarksi microscopy to observe the recently laid eggs. In the case of the wild-type worm strain, the eggs were laid during gastrulation (28 cells) or up to a cell stage consisting of 50 cells (beginning of morphogenesis). FIG. 8 shows two eggs which were laid by Parkin KO2 worms.

Results:

Some of the eggs laid by the Parkin KO2 worm strain are in a cell stage which is too far advanced. Parkin KO2 consequently suffers from a partial egglaying defect (egl). This defect was also observed in the case of the Parkin KO1 worm strain.

d) Number of Descendants

Method:

10 eggs were isolated individually per worm strain tested. As soon as the individuals developing from these eggs laid eggs once again, the worms were changed in a 24-hour rhythm until no more eggs were laid. The descendants were counted in the L1/L2 stage. In this way, it was possible to count all the descendants. Furthermore, it was possible to outline the chronological course of the egglaying in the same experiment.

Figure 9:
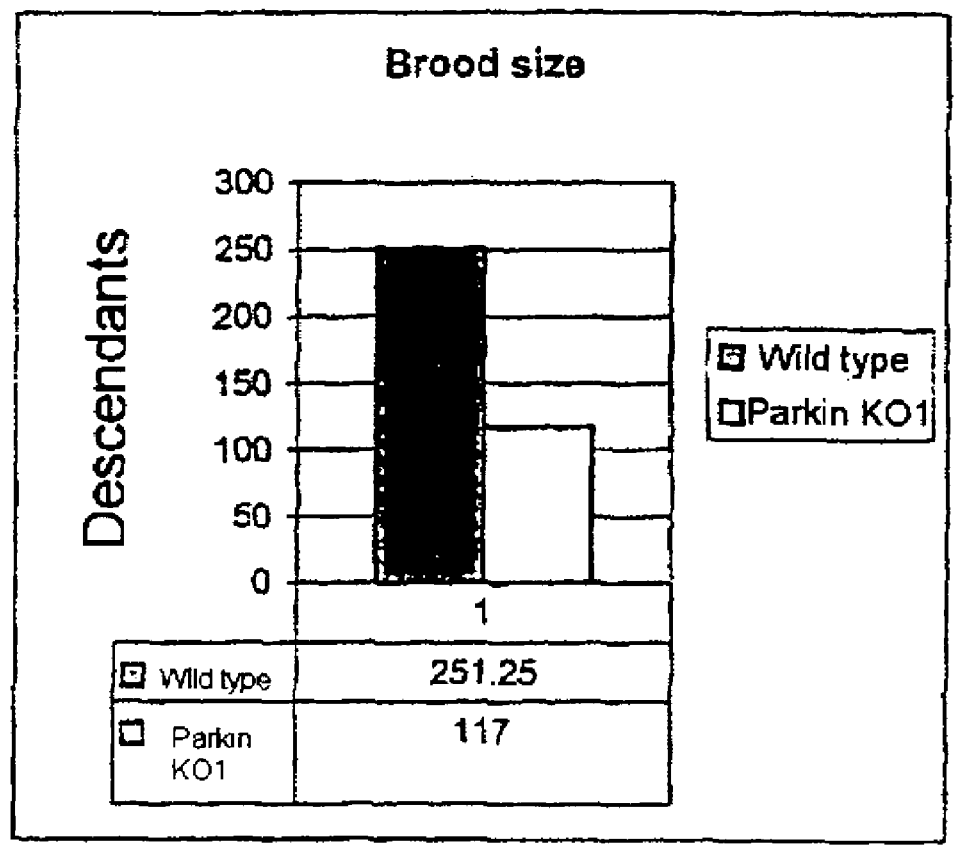
FIG. 9: Size of the descendants and number of the eggs which were laid by Parkin KO1 worms.

Results:

The result is shown in FIG. 9.

e) Determining the Sinusoidal Curve for Testing Mobility

Method:

5 young adult worms were deposited on a fresh plate. The amplitude and sinusoidal length of the sinusoidal track left behind in the bacterial lawn were then measured by way of a visual display. 10 tracks were traced on film, which was then overlaid.

Results:

The sinusoidal amplitude in the case of the Parkin KO1 and KO2 worm strains corresponded approximately to the wild-type amplitude. However, the sinusoidal length was approx. 20% shorter than in the case of the the wild-type worm strains. The mobility of the Parkin KO1 and KO2 worm strains was consequently disrupted (unc).

f) Defacation

Method:

The periods between the expulsion and between pBoc (intestinal contraction shortly before the expulsion) and the subsequent expulsion were measured. 10 animals were observed per worm strain.

Results:

Both the expulsion-expulsion cycle and the pBoc expulsion cycle were shorter in Parkin KO1 and Parkin KO2 than in the wild type.

11. Complementing the *C. elegans* Gene with the Homologous Human Gene

In order to carry out the detailed molecular characterization of the mutants, they were subjected to a function test. Tests were carried out to determine whether the phenotypes really were to be attributed to the deletion in the target gene, on the one hand, and, on the other hand, whether the *C. elegans* target gene and the human target gene were functionally conserved. For this reason, the deleted *C. elegans* target gene itself, on the one hand, and the homologous human gene, on the other hand, were in each case inserted into the *C. elegans* knock-out strains possessing the deletions in the target genes. Both genes were employed as cDNA constructs containing the *C. elegans* promoter (FIG. 2) in order to ensure a pattern of expression which corresponded to that of the target gene. An is injection microscope (Zeiss) was used to introduce the constructs directly into the worm as plasmids (50 ng/µl). The defects in chemotaxis, development, egglaying, defacation and mobility were able to be reversed both by introducing the *C. elegans* Parkin and by introducing the human Parkin.

12. RNAi Experiment Using the *C. elegans* Parkin Gene

Figure 5:
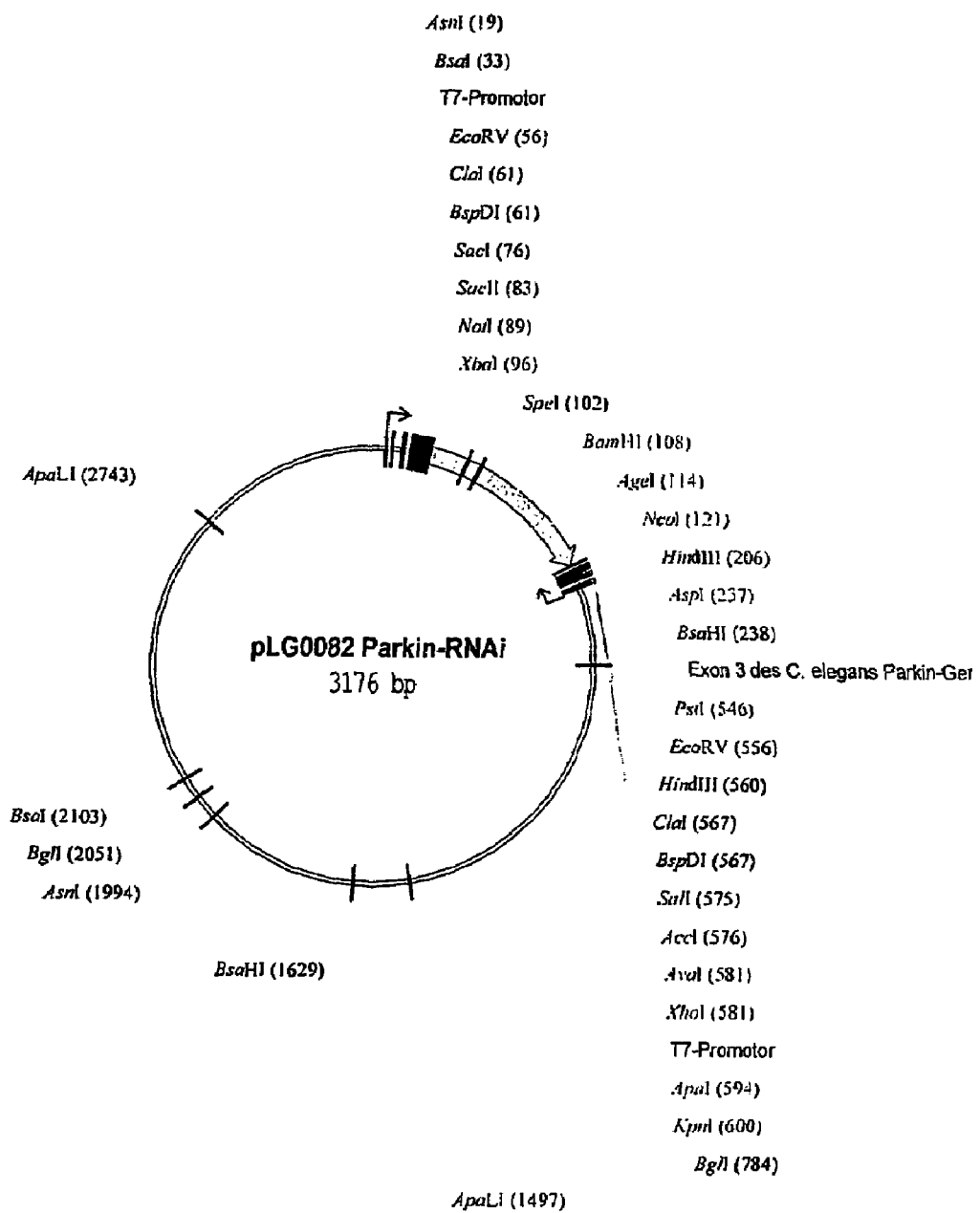
FIG. 5: Plasmid pLG0082 (SEQ ID NO:4), which contains exon 3 of the C. elegans Parkin gene and was used for the RNAi experiments (cf. experimental section 12.).

For the purpose of carrying out an RNAi feeding experiment for inactivating the Parkin gene, the plasmid pLG0082 (see FIG. 5) was first of all constructed: a 441 bp DNA fragment constituting a part of exon 3 of the Parkin gene was prepared by PCR amplification using the oligonucleotides 1-RNA1 and 1-RNA2. The choice of the oligonucleotides resulted in the introduction of an NcoI restriction cleavage site at the 5' end and a PstI restriction cleavage site at the 3' end. After the PCR fragment had been isolated, it was cut with the corresponding restriction enzymes and ligated into the vector pPD129.36 (Dr. Andrew Fire, Carnegie Institution of Washington, Baltimore, Md., USA), which had been digested with the same enzymes. In this way, the Parkin fragment was positioned between two T7 RNA polymerase promoters.

The *E. coli* strain HT115 (Dr. Lisa Timmons, Carnegie Institution of Washington, Baltimore, Md., USA) was transformed with the plasmid pLG0082 and ampicillin-resistant colonies were isolated. This strain carries a chromosomal copy of the gene for T7 RNA polymerase under the control of a lacZ promoter and therefore produces both sense RNA and antisense RNA corresponding to exon 3 of the Parkin gene following induction with 1 mM IPTG. Growth of the worms on these bacteria leads to the worms taking up the double-stranded Parkin RNA and to the Parkin gene being inactivated as a result.

Per experiment, five wild-type worms in the L3 stage of development were reared on these feed bacteria at 15° C. for about 2-3 days. Following a change to 20° C., their descendants were subsequently analyzed phenotypically.

```
1-RNA1:   CAGACAAACCATGGTTCTCC    (SEQ ID NO:9)

1-RNA2:   CTTACTCTGCAGCAGAATTGG   (SEQ ID NO:10)
```

Defects in egglaying, defacation and mobility were observed.

13. Preparing a *C. elegans* Mutant which Expresses Human α-synuclein

Cloning the Constructs

In order to prepare the constructs which express α-synuclein under the control of the unc-119 promoter, human α-synuclein cDNA (Dr. Christian Haass, Ludwig-Maximilians University Munich) and the cDNAs of the A53T and A30P mutants (Dr. Christian Haass, Ludwig-Maximilians University Munich) were amplified by PCR using primers which contained cleavage sites for SalI. The amplified and cut DNA fragments were cloned into the SalI cleavage sites of the vector pPD49.24 (Dr. Andrew Fire, Carnegie Institution of Washington, Baltimore, Md., USA), into which the promoter of the *C. elegans* unc-119 gene had previously been introduced. The 5' promoter region upstream of the unc-119 gene had been amplified by means of PCR and two primers from the cosmid M142. This gave rise to constructs pBY456 (unc-119::α-synuclein wt), pBY457 (unc-119::α-synuclein A53T) and pBY458 (unc-119::α-synuclein A30P).

In order to prepare the constructs which express α-synuclein under the control of the sel-12 promoter, human α-synuclein cDNA and the cDNAs of the A53T and A30P mutants were excised from the constructs pBY456, pBY457 and pBY458, respectively, using the restriction enzymes MscI and NcoI and cloned into the MscI/NcoI incision sites of the vector pPD49.26 (Dr. Andrew Fire, Carnegie Institution of Washington, Baltimore, Md., USA), into which the promoter of the *C. elegans* sel-12 gene have previously been introduced. The 5'promoter region upstream of the sel-12 gene was amplified by means of PCR and the two primers RB759 and RB110 (see below) from the cosmid C08A12. This gave rise to the constructs pBY1158 (sel-12::α-synuclein wt), pBY1159 (sel-12::α-synuclein A53T) and pBY1160 (sel-12::α-xynuclein A30P).

```
RB759:
CCCGGCTGCAGCTCAATTATTCTAGTAAGC      (SEQ ID NO:11)

RB110:
GTCTCCATGGATCCGAATTCTGAAACGT-       (SEQ ID NO:12)
TCAAATAAC
```

The unc-119 promoter gave rise to panneuronal expression whereas expression in the case of the sel-12 promoter took place neuronally and in some muscle cells.

Preparing Transgenic Animals

Transgenes were introduced into *C. elegans* by microinjecting them into the gonads (Mello et al., 1992). The above-described α-synuclein constructs were coinjected together with the marker plasmids pBY1153 (sel-12:: EGFP) and pBY266 (dat::EGFP), respectively, and GFP-expressing descendants were selected.

Strains which possess the transgene stably integrated in the chromosome were obtained by X-irradation (5000 rad) of lines which harbored the transgenic, extrachromosomal arrays. The descendants of the X-irradiated animals were screened for 100% transmission of the transgenic marker. In order to eliminate any possible background mutations, the integrated lines were backcrossed with wild-type worms (N2).

PAGE and Immunoblotting

The proteins were extracted from *C. elegans*, and PAGE and Western blotting were carried out, as described by Okochi et al. (2000). The monoclonal antibody 15G7 (Connex, Martinsried) was used, diluted 1:4, for immunostaining of the Western blots. The secondary antibody employed was a peroxidase-conjugated goat a rat antibody (Jackson) which was diluted 1:5000.

Immunostainings

The immunostainings were carried out in accordance with a standard protocol (Finny et al. 1990) using the monoclonal antibody 15G7 (Connex, Martinsried) in the undiluted state. The secondary antibody employed was a Texas red-coupled goat α rat antibody diluted 1:2000.

α-Synuclein Aggregations in Urea Extracts in Vitro

Figure 10:
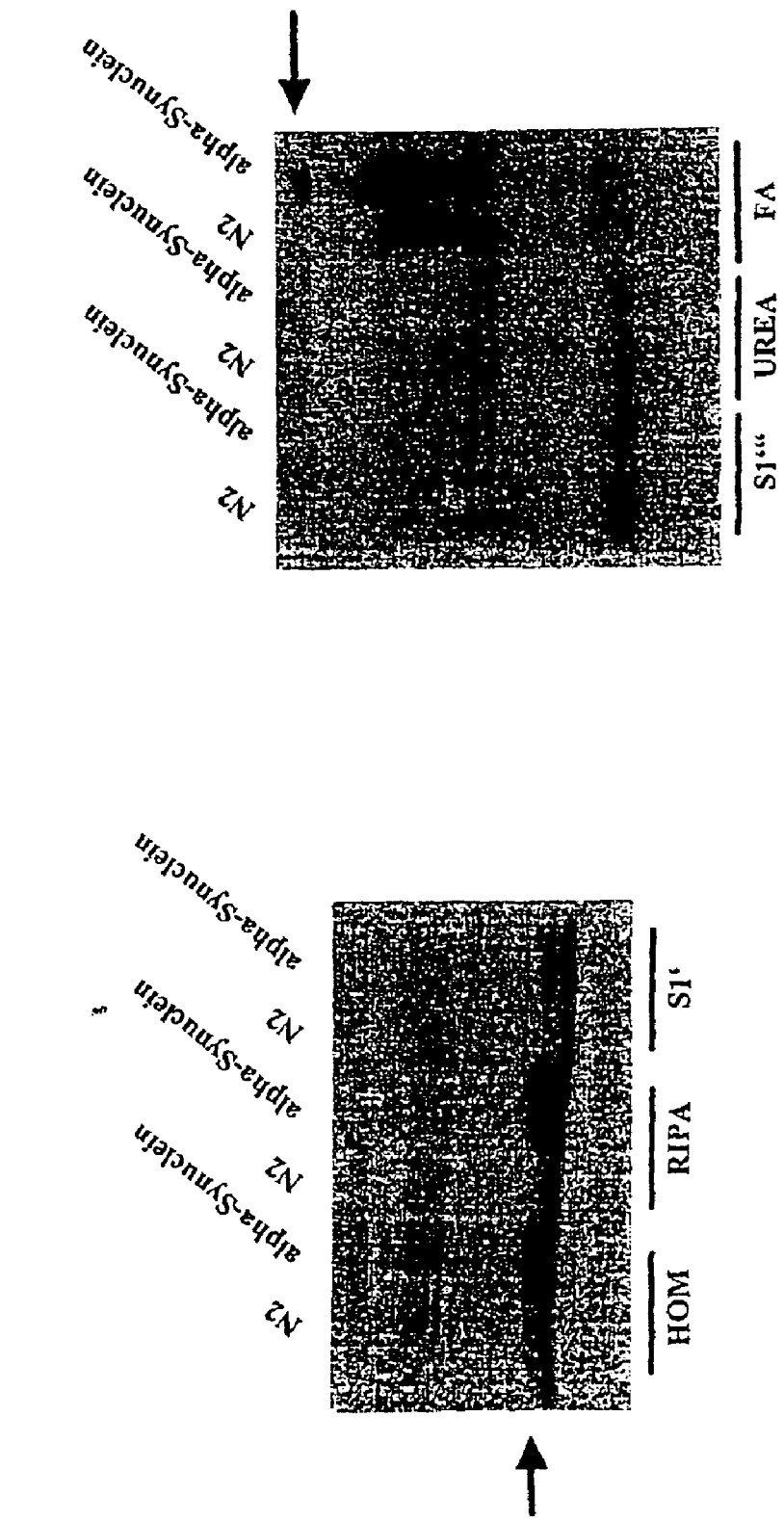
FIG. 10: Western blot of extracts from wild-type worms (N2) and worms which are expressing human α-synuclein A30P, which was integrated into the genome and under the control of the sel-12 promoter. The different fractions from the protein extraction are indicated below the blot: HOM, homogenate; RIPA, RIPA-soluble fraction; S1', first washing step with 5% SDS; S1''', third washing step with 5% SDS; UREA, urea-soluble fraction; FA, formic acid-soluble frction. Black arrows denote the α-synuclein-specific bands.

In a Western blot (FIG. 10) using a monoclonal antibody directed against α-synuclein, yeast extracts of proteins from the integrated sel-12/α-synuclein A30P worm exhibit a high molecular weight band which is not visible in N2 worm extracts which have been treated in the same way.

α-Synuclein Aggregations in Neurons in Vivo

Figure 11:
FIG. 11: Analysis of transgenic worms which are expressing α-synuclein A30P as an extrachromosomal array under the control of the unc-119 promoter. The immunostaining (A) was carried out using the monoclonal antibody 15G7. (B) Expression of GFP under the control of the dat promoter. (C) DAPI staining; (D) Nomarski micrograph.

The immunostainings (FIG. 11) of unc-119/α-synuclein A30P using a monoclonal antibody directed against α-synuclein exhibit clear signals, both in the cell body and in axons, with pearl necklace-like staining frequently being seen in the latter. This points to the α-synuclein protein being transported to the presynapse and to the protein being accumulated in the axons.

Defects in Egglaying and in Vulva Formation

Worms in which the sel-12/α-synuclein A30P construct is stably integrated into the genome exhibit deformation of the vulva (p-vul) and a defect in egglaying (egl) (FIG. 12).

REFERENCES

1. Polymeropoulos, M. H. et al. Mutation in the alpha-synuclein gene identified in families with Parkinson's disease [see comments]. *Science* 276, 2045-7 (1997).
2. Kitada, T. et al. Mutations in the parkin gene cause autosomal recessive juvenile parkinsonism [see comments]. *Nature* 392, 605-8 (1998).
3. Baumeister, R., Liu, Y. & Ruvkun, G. Lineage-specific regulators couple cell lineage asymmetry to the transcription of the *C.elegans* POU gene unc-86 during neurogenesis. *Genes Dev.* 10, 1395-1410 (1996).
4. Way, J. C. & Chalfie, M. The mec-3 gene of Caenorhabditis elegans requires its own product for maintained expression and is expressed in three neuronal cell types. *Genes Dev.* 3, 1823-1833 (1989).
5. Hobert, O. et al. Regulation of interneuron function in the *C. elegans* thermoregulatory pathway by the ttx-3 LIM homeobox gene. *Neuron* 19, 345-57 (1997).
6. Dunnett, S. B. and Björklund, A. Prospects for new restorative and neuroprotective treatments in Parkinson's disease. *Nature* 399, A32-A39 (1999).

7. Hattori, N. et al. Molecular genetic analysis of a novel Parkin gene in Japanese families with autosomal recessive juvenile Parkinsonism: evidence for variable homozygous deletions in the Parkin gene in affected individuals. Ann. Neurol. 44, 935-941 (1998).
8. Liu, L. X. et al. High-throughput isolation of Caenorhabditis elegans deletion mutants. *Genome Res*. 9, 859-867 (1999).
9. Olanow, C. W. and Tatton, W. G. Etiology and pathogenesis of Parkinson's disease. *Annu Rev. Neurosci*. 22, 123-144 (1999).
10. Yandell, M. D., Edgar, L. G. and Wood, W. B. Trimethylpsoralen induces small deletion mutations in *Caenorhabditis elegans*. *Proc. Natl. Acad. Sci*. 91, 1381-1385 (1994).
11. Clayton, D. F. and George, J. M. The synuclein: a family of proteins involved in synaptic function, plasticity, neurodegeneration and disease. *TINS* 21, 249-254 (1998).
12. Giasson, B. I., Murray, I., Trojanowski, J. Q. and Lee, V. M. A hydrophobic stretch of 12 amino acid residues in the middle of alpha-synuclein is essential for filament assembly. *J. Biol. Chem*. 26, 2380-2386 (2000).
13. Feany, M. B. and Bender, W. W. A parkinson model of parkinson's disease. *Nature* 404, 394-398 (2000).
14. Finney, M. and Ruvkun, G. The unc-86 gene product couples cell lineage and cell identity in *C. elegans*. *Cell* 63, 895-905 (1990).
15. Kruger, R. et al. Ala30Pro mutation in the gene encoding alpha-synuclein in Parkinson's disease. *Nat Genet*. 18, 106-8 (1998).
16. Masliah, E. et al. Dopaminergic loss and inclusion body formation in alpha-synuclein mice: implication for neurodegenerative disorders. *Science* 287, 1265-1269 (2000).
17. Mello, C. C., Kramer, J. M., Stinchcomb, D. and Ambros, V. Efficient gene transfer in *C. elegans*. Extrachromosomal maintainance and integration of transforming sequences. *EMBO J*. 10, 3959-3970 (1992).
18. Okochi, M. et al. A loss of function mutant of the presenilin homologue SEL-12 undergoes aberrant endoproteolysis in caenorhabditis elegans and increases abeta 42 generation in human cells. *J. Biol. Chem*. 275, 40925-32 (2000).
19. Zamore, P. D. et al., RNAi.: Double-stranded RNA directs the ATP-dependent cleavage of mRNA at 21 to 23 nucleotide intervals. Cell 101, 25-33 (2000).

The invention claimed is:

1. A genetically modified nematode belonging to genus *Caenorhabditis* comprising Parkin gene K08E3.7, wherein the expression of said Parkin gene is nonexistent.

2. The genetically modified nematode as in claim 1, wherein the nonexistent Parkin gene expression produces plaque-like deposits in the nervous system of the genetically modified nematode.

3. The genetically modified nematode as in claim 1, further comprising a phenotype associated with the nonexistent expression of said Parkin gene selected from the group consisting of:
 a defect in chemotaxis;
 a defect in egglaying;
 an extended period of development;
 a decreased number of descendants;
 problems in coordination;
 a defect in defecation;
 retarded locomotion; and
 a reduced body length.

4. The genetically modified nematode as in claim 1, wherein said Parkin gene is partially or entirely deleted.

5. The genetically modified nematode as in claim 1, wherein said Parka gene is mutated.

6. The genetically modified nematode as in claim 1, wherein said Parkin gene has been inactivated at least transiently by means of the RNA interference technique.

7. The genetically modified nematode as in claim 1, further comprising a transgene.

8. The genetically modified nematode as in claim 1, wherein said nematode belongs to the species selected from the group consisting of: *elegans, vulgaris*, and *briggsae*.

9. The genetically modified nematode as in claim 1, wherein said nematode is *Caenorhabditis elegans*.

* * * * *

SEQUENCE LISTING

```
<160> NUMBER OF SEQ ID NOS: 12

<210> SEQ ID NO 1
<211> LENGTH: 1161
<212> TYPE: DNA
<213> ORGANISM: Caenorhabditis elegans
<220> FEATURE:
<221> NAME/KEY: CDS
<222> LOCATION: (1)..(1158)

<400> SEQUENCE: 1 atg tct gat gaa atc tct ata tta ata caa gat aga aaa aca ggt caa    48
Met Ser Asp Glu Ile Ser Ile Leu Ile Gln Asp Arg Lys Thr Gly Gln
 1               5                  10                  15 cgt agg aat cta aca ctt aat ata aat ata act gga aat atc gaa gat    96
Arg Arg Asn Leu Thr Leu Asn Ile Asn Ile Thr Gly Asn Ile Glu Asp
             20                  25                  30 ctc aca aaa gat gtg gaa aag ctc acc gaa att ccc agc gat gag ctg   144
Leu Thr Lys Asp Val Glu Lys Leu Thr Glu Ile Pro Ser Asp Glu Leu
         35                  40                  45 gaa gtg gtt ttc tgt ggg aaa aag tta tca aaa tca acg att atg agg   192
Glu Val Val Phe Cys Gly Lys Lys Leu Ser Lys Ser Thr Ile Met Arg
     50                  55                  60 gat ttg tca ctg aca cct gca aca caa atc atg ctt ctc cgt cca aag   240
Asp Leu Ser Leu Thr Pro Ala Thr Gln Ile Met Leu Leu Arg Pro Lys
 65                  70                  75                  80 ttc aat agt cac aac gaa aac ggt gct act act gca aaa ata aca aca   288
Phe Asn Ser His Asn Glu Asn Gly Ala Thr Thr Ala Lys Ile Thr Thr
                 85                  90                  95 gat tct tca att ctc gga agc ttc tac gtg tgg tgc aaa aat tgt gac   336
Asp Ser Ser Ile Leu Gly Ser Phe Tyr Val Trp Cys Lys Asn Cys Asp
            100                 105                 110 gac gtc aag cgc ggc aaa ctg cgg gtt tat tgc caa aaa tgc tcg tca   384
Asp Val Lys Arg Gly Lys Leu Arg Val Tyr Cys Gln Lys Cys Ser Ser
        115                 120                 125 acc tct gtt cta gtc aaa tct gaa ccc cag aac tgg tcc gac gtt ctc   432
Thr Ser Val Leu Val Lys Ser Glu Pro Gln Asn Trp Ser Asp Val Leu
    130                 135                 140 aaa agc aag aga ata ccg gcg gtc tgc gaa gaa tgc tgt act cca ggt   480
Lys Ser Lys Arg Ile Pro Ala Val Cys Glu Glu Cys Cys Thr Pro Gly
145                 150                 155                 160 ctt ttc gct gaa ttc aag ttc aaa tgt cta gcc tgc aac gat ccg gcc   528
Leu Phe Ala Glu Phe Lys Phe Lys Cys Leu Ala Cys Asn Asp Pro Ala
                165                 170                 175 gca gct cta act cac gta cgc gga aat tgg caa atg acc gag tgc tgt   576
```

```
                Ala Ala Leu Thr His Val Arg Gly Asn Trp Gln Met Thr Glu Cys Cys
                            180                 185                 190
gtt tgt gat ggg aag gag aaa gtg atc ttc gac ctc gga tgc aat cat         624
Val Cys Asp Gly Lys Glu Lys Val Ile Phe Asp Leu Gly Cys Asn His
        195                 200                 205
att aca tgc caa ttc tgt ttc aga gat tat ttg cta agt caa ctg gaa         672
Ile Thr Cys Gln Phe Cys Phe Arg Asp Tyr Leu Leu Ser Gln Leu Glu
    210                 215                 220
cga ttc ggt ttt gtc aat cag ccg ccg cat ggc ttc acc att ttc tgc         720
Arg Phe Gly Phe Val Asn Gln Pro Pro His Gly Phe Thr Ile Phe Cys
225                 230                 235                 240
ccc tat cca ggg tgc aat aga gtg gta caa gat gtg cac cat ttc cac         768
Pro Tyr Pro Gly Cys Asn Arg Val Val Gln Asp Val His His Phe His
                245                 250                 255
att atg ggt cag acg tcg tac agc gaa tac caa cgg aaa gcc acc gag         816
Ile Met Gly Gln Thr Ser Tyr Ser Glu Tyr Gln Arg Lys Ala Thr Glu
            260                 265                 270
cga ttg att gcc gtg gac gac aag ggt gtg act tgc ccg aat gtc tcg         864
Arg Leu Ile Ala Val Asp Asp Lys Gly Val Thr Cys Pro Asn Val Ser
        275                 280                 285
tgt ggg cag agc ttc ttc tgg gag ccc tat gat gac gat gga aga tcc         912
Cys Gly Gln Ser Phe Phe Trp Glu Pro Tyr Asp Asp Asp Gly Arg Ser
    290                 295                 300
cag tgt cca gat tgt ttt ttt tcg ttt tgc aga aag tgc ttc gaa aga         960
Gln Cys Pro Asp Cys Phe Phe Ser Phe Cys Arg Lys Cys Phe Glu Arg
305                 310                 315                 320
aat tgt gtg tgc cag agc gaa gac gat ctc acc cga act aca att gac        1008
Asn Cys Val Cys Gln Ser Glu Asp Asp Leu Thr Arg Thr Thr Ile Asp
                325                 330                 335
gcg act aca aga aga tgc cca aaa tgc cac gtg gca acc gaa cgg aac        1056
Ala Thr Thr Arg Arg Cys Pro Lys Cys His Val Ala Thr Glu Arg Asn
            340                 345                 350
ggc gga tgt gct cac att cac tgt acc tcg tgt gga atg gat tgg tgt        1104
Gly Gly Cys Ala His Ile His Cys Thr Ser Cys Gly Met Asp Trp Cys
        355                 360                 365
ttc aag tgc aag aca gaa tgg aag gaa gag tgt caa tgg gac cat tgg        1152
Phe Lys Cys Lys Thr Glu Trp Lys Glu Glu Cys Gln Trp Asp His Trp
    370                 375                 380
ttt aat taa                                                            1161
Phe Asn
385

<210> SEQ ID NO 2
<211> LENGTH: 386
<212> TYPE: PRT
<213> ORGANISM: Caenorhabditis elegans

<400> SEQUENCE: 2

Met Ser Asp Glu Ile Ser Ile Leu Ile Gln Asp Arg Lys Thr Gly Gln
  1               5                  10                  15
Arg Arg Asn Leu Thr Leu Asn Ile Asn Ile Thr Gly Asn Ile Glu Asp
                 20                  25                  30
Leu Thr Lys Asp Val Glu Lys Leu Thr Glu Ile Pro Ser Asp Glu Leu
             35                  40                  45
Glu Val Val Phe Cys Gly Lys Lys Leu Ser Lys Ser Thr Ile Met Arg
         50                  55                  60
Asp Leu Ser Leu Thr Pro Ala Thr Gln Ile Met Leu Leu Arg Pro Lys
 65                  70                  75                  80
Phe Asn Ser His Asn Glu Asn Gly Ala Thr Thr Ala Lys Ile Thr Thr
                 85                  90                  95
Asp Ser Ser Ile Leu Gly Ser Phe Tyr Val Trp Cys Lys Asn Cys Asp
            100                 105                 110
Asp Val Lys Arg Gly Lys Leu Arg Val Tyr Cys Gln Lys Cys Ser Ser
        115                 120                 125
Thr Ser Val Leu Val Lys Ser Glu Pro Gln Asn Trp Ser Asp Val Leu
    130                 135                 140
Lys Ser Lys Arg Ile Pro Ala Val Cys Glu Glu Cys Cys Thr Pro Gly
145                 150                 155                 160
Leu Phe Ala Glu Phe Lys Phe Lys Cys Leu Ala Cys Asn Asp Pro Ala
                165                 170                 175
Ala Ala Leu Thr His Val Arg Gly Asn Trp Gln Met Thr Glu Cys Cys
            180                 185                 190
Val Cys Asp Gly Lys Glu Lys Val Ile Phe Asp Leu Gly Cys Asn His
        195                 200                 205
Ile Thr Cys Gln Phe Cys Phe Arg Asp Tyr Leu Leu Ser Gln Leu Glu
    210                 215                 220
Arg Phe Gly Phe Val Asn Gln Pro Pro His Gly Phe Thr Ile Phe Cys
```

```
225                 230                 235                 240
Pro Tyr Pro Gly Cys Asn Arg Val Val Gln Asp Val His His Phe His
                245                 250                 255
Ile Met Gly Gln Thr Ser Tyr Ser Glu Tyr Gln Arg Lys Ala Thr Glu
                260                 265                 270
Arg Leu Ile Ala Val Asp Asp Lys Gly Val Thr Cys Pro Asn Val Ser
            275                 280                 285
Cys Gly Gln Ser Phe Phe Trp Glu Pro Tyr Asp Asp Gly Arg Ser
        290                 295                 300
Gln Cys Pro Asp Cys Phe Phe Ser Phe Cys Arg Lys Cys Phe Glu Arg
    305                 310                 315                 320
Asn Cys Val Cys Gln Ser Glu Asp Asp Leu Thr Arg Thr Thr Ile Asp
                325                 330                 335
Ala Thr Thr Arg Arg Cys Pro Lys Cys His Val Ala Thr Glu Arg Asn
                340                 345                 350
Gly Gly Cys Ala His Ile His Cys Thr Ser Cys Gly Met Asp Trp Cys
            355                 360                 365
Phe Lys Cys Lys Thr Glu Trp Lys Glu Glu Cys Gln Trp Asp His Trp
        370                 375                 380
Phe Asn
385

<210> SEQ ID NO 3
<211> LENGTH: 6451
<212> TYPE: DNA
<213> ORGANISM: Artificial Sequence
<220> FEATURE:
<223> OTHER INFORMATION: Description of Artificial Sequence: Plasmid
      pLG0126

<400> SEQUENCE: 3
cgatatcgaa cattgccagc ttcttgcgag cttttctgaa ataatagtgt tttctaaaca   60
cgtaaacatg aaatatttca cttacgcaag tgcttcttcg gcctctctca tatctgcatt  120
cagccgcttt ttggattcct cggaatcttt ccacagcttg cggagacgct caatctcatc  180
aatcaaatga aacattcctg aaacacgtca ttaaaatttg aaaatgataa ttgaaactaa  240
cctatatcct taatatcgaa ttgcggtcgc tgtgagttta gaatcatgtt gaaaatgtga  300
cgcgagtttt cgccgcacac cttctctttt gatgtactgg acttcattct aaaatgtgga  360
aatgattaga aaacgagaaa ctcgcccgaa ataagagaa aaatgcgtga aaccgtttc   420
aaatttcgtg gaaaacagtt cgaatttgaa gctcgctgcg tttgtctcac acgcgacgcg  480
acccgctacg cttgccatag ggcgcacatg actgcgagga ctagtgtgca caaaaacatg  540
gggcttcaag gcctcgacta gtttttttgaa tttaatgttt aaaactgcaa gcaggcccgc  600
tagcaggaaa ttttttttgtt aatttctaag tcaaattttc agctctcatg aagcatgtct  660
gatgaaatct ctatattaat acaagataga aaaacaggtc aacgtaggaa tctaacactt  720
aatgtagtgg acatttcaaa cttttgaatat atacattatt tttttcagat aaatataact  780
ggaaatatcg aagatctcac aaaagatgtg gaaaagctca ccgaaattcc cagcgatgag  840
ctggaagtgg ttttctgtgg gaaaaagtta tcaaaatcaa cgattatgag ggatttgtca  900
ctgacacctg caacgtaggt caagtaaata tttacttata taaataactg gaattgttat  960
ttatataaat aactggaatt gttattcaaa taatattatt tcagacaaat catgcttctc 1020
cgtccaaagt tcaatagtca caacgaaaac ggtgctacta ctgcaaaaat aacaacagat 1080
tcttcaattc tcggaagctt ctacgtgtgg tgcaaaaatt gtgacgacgt caagcgcggc 1140
aaaactgcgg tttattgcca aaaatgctcg tcaacctctg ttctagtcaa atctgaaccc 1200
cagaactggt ccgacgttct caaaagcaag agaatacggc cggtctgcga agaatgctgt 1260
actccaggtc ttttcgctga attcaagttc aaatgtctag cctgcaacga tccggccgca 1320
gctctaactc acgtacgcgg aaattggcaa atgaccgagt gctgtgtttg tgatgggaag 1380
gagaaagtga tcttcgacct cggatgcaat catattcat gccaattctg tttcagagtg 1440
agtaagaatc taaattttt gttgaaattg tttaattta aaggattatt tgctaagtca 1500
actggaacga ttcggttttg tcaatcagcc gccgcatggc ttcaccattt tctgccccta 1560
tccagggtgc aatagttcgt tcgatttttat caaaaccatt caattttctg cagtagtgat 1620
cctgaaaact aattgataga aacaaaaaat cttccaaaaa atacaaatat gttatgtttc 1680
catttgcaa gtctggcatg gttttttttt tgcaaaaaaa acccccaccc gttctattta 1740
aatttatttt gaaaatttttc tcacatgttt caatagtttt tcaatgccga gaaaattgaa 1800
aaaaaaagtt ttaaagaaat taaacagaac atttaattga aaaataactt caggagtggt 1860
acaagatgtg caccatttcc acattatggg tcagacgtcg tacagcgaat ccaacggaa  1920
agccaccgag cgattgattg ccgtggacga caagggtgtg acttgcccga atgtctcgtg 1980
tgggcagagc ttcttctggg agccctatga tgacgattga agatcccagt gtccagatga 2040
ttttttttcg ttttgcaggt attttgagct tctaaatcgg aaattttatc gcaataaata 2100
tcatcgttca gaaagtgctt cgaaagaaat tgtgtgtgcc agagcgaaga cgatctcacc 2160
cgaactacaa ttgacgcgac tacaaggtga tctcagcgat tatccactac aaaaaactgt 2220
aaattcttcc agaagatgcc caaaatgcca cgtggcaacc cggcgatgtc gcggatgtgc 2280
tcacattcac tgtacctcgt gtggaatgga ttggtgtttc aagtgcaaga cagaatggaa 2340
ggaagagtgt caatgggacc attggtttaa taggtcgacg gtaccgcggg cccgggatcc 2400
accggtcgcc accatggtga gcaagggcga ggagctgttc accggggtgg tgcccatcct 2460
ggtcgagctg gacggcgacg taaacggcca caagttcagc gtgtccggcg agggcgaggg 2520
cgatgccacc tacggcaagc tgaccctgaa gttcatctgc accaccggca agctgcccgt 2580
gccctggccc accctcgtga ccaccctgac ctacggcgtg cagtgcttca gccgctaccc 2640
cgaccacatg aagcagcacg acttcttcaa gtccgccatg cccgaaggct acgtccagga 2700
gcgcaccatc ttcttcaagg acgacggcaa ctacaagacc cgcgccgagg tgaagttcga 2760
```

```
gggcgacacc ctggtgaacc gcatcgagct gaagggcatc gacttcaagg aggacggcaa 2820
catcctgggg cacaagctgg agtacaacta caacagccac aacgtctata tcatggccga 2880
caagcagaag aacggcatca aggtgaactt caagatccgc cacaacatcg aggacggcag 2940
cgtgcagctc gccgaccact accagcagaa cacccccatc ggcgacggcc ccgtgctgct 3000
gcccgacaac cactacctga gcacccagtc cgccctgagc aaagacccca acgagaagcg 3060
cgatcacatg gtcctgctgg agttcgtgac cgccgccggg atcactctcg gcatggacga 3120
gctgtacaag taaagcggcc gccaccgcgg tggagctccg catcggccgc tgtcatcaga 3180
tcgccatctc gcgcccgtgc ctctgacttc taagtccaat tactcttcaa catccctaca 3240
tgctctttct ccctgtgctc ccaccccta ttttgttat tatcaaaaaa acttcttctt 3300
aatttctttg tttttagct tcttttaagt cacctctaac aatgaaattg tgtagattca 3360
aaaatagaat taattcgtaa taaaaagtcg aaaaaaattg tgctccctcc ccccattaat 3420
aataattcta tcccaaaatc tacacaatgt tctgtgtaca cttcttatgt ttttttact 3480
tctgataaat ttttttgaa acatcataga aaaaccgca cacaaaatac cttatcatat 3540
gttacgtttc agtttatgac cgcaattttt atttcttcgc acgtctgggc ctctcatgac 3600
gtcaaatcat gctcatcgtg aaaaagtttt ggagtatttt tggaattttt caatcaagtg 3660
aaagtttatg aaattaattt tcctgctttt gcttttggg ggttcccct attgtttgtc 3720
aagagtttcg aggacggcgt ttttcttgct aaaatcacaa gtattgatga gcacgatgca 3780
agaaagatcg gaagaaggtt tgggtttgag gctcagtgga aggtgagtag aagttgataa 3840
tttgaaagtg gagtagtgtc tatgggtttt ttgccttaaa tgacagaata cattcccaat 3900
ataccaaaca taactgtttc ctactagtcg gccgtacggg ccctttcgtc tcgcgcgttt 3960
cggtgatgac ggtgaaaacc tctgacacat gcagctcccg gagacggtca cagcttgtct 4020
gtaagcggat gccgggagca gacaagcccg tcagggcgcg tcagcgggtg ttggcggtg 4080
tcggggctgg cttaactatg cggcatcaga gcagattgta ctgagagtgc accatatgcg 4140
gtgtgaaata ccgcacagat gcgtaaggag aaaataccgc atcaggcggc cttaagggcc 4200
tcgtgatacg cctattttta taggttaatg tcatgataat aatggtttct tagacgtcag 4260
gtggcacttt tcggggaaat gtgcgcggaa cccctatttg tttatttttc taaatacatt 4320
caaatatgta tccgctcatg agacaataac cctgataaat gcttcaataa tattgaaaaa 4380
ggaagagtat gagtattcaa catttccgtg tcgcccttat tcccttttt gcggcatttt 4440
gccttcctgt ttttgctcac ccagaaacgc tggtgaaagt aaaagatgct gaagatcagt 4500
tgggtgcacg agtgggttac atcgaactgg atctcaacag cggtaagatc cttgagagtt 4560
ttcgccccga agaacgtttt ccaatgatga gcacttttaa agttctgcta tgtggcgcgg 4620
tattatcccg tattgacgcc gggcaagagc aactcggtcg ccgcatacac tattctcaga 4680
atgacttggt tgagtactca ccagtcacag aaaagcatct tacggatggc atgacagtaa 4740
gagaattatg cagtgctgcc ataaccatga gtgataacac tgcggccaac ttacttctga 4800
caacgatcgg aggaccgaag gagctaaccg cttttttgca caacatgggg gatcatgtaa 4860
ctcgccttga tcgttgggaa ccggagctga atgaagccat accaaacgac gagcgtgaca 4920
ccacgatgcc tgtagcaatg gcaacaacgt tgcgcaaact attaactggc gaactactta 4980
ctctagcttc ccggcaacaa ttaatagact ggatggaggc ggataaagtt gcaggaccac 5040
ttctgcgctc ggcccttccg gctggctggt ttattgctga taaatctgga gccggtgagc 5100
gtgggtctcg cggtatcatt gcagcactgg ggccagatgg taagccctcc cgtatcgtag 5160
ttatctacac gacgggagt caggcaacta tggatgaacg aaatagacag atcgctgaga 5220
taggtgcctc actgattaag cattggtaac tgtcagacca agtttactca tatatacttt 5280
agattgattt aaaacttcat ttttaattta aaaggatcta ggtgaagatc ctttttgata 5340
atctcatgac caaaatccct taacgtgagt tttcgttcca ctgagcgtca gaccccgtag 5400
aaaagatcaa aggatcttct tgagatcctt ttttctgcg cgtaatctgc tgcttgcaaa 5460
caaaaaaacc accgctacca gcggtggttt gtttgccgga tcaagagcta ccaactcttt 5520
ttccgaaggt aactggcttc agcagagcgc agataccaaa tactgtcctt ctagtgtagc 5580
cgtagttagg ccaccacttc aagaactctg tagcaccgcc tacatacctc gctctgctaa 5640
tcctgttacc agtggctgct gccagtggcg ataagtcgtg tcttaccggg ttggactcaa 5700
gacgatagtt accggataag gcgcagcggt cgggctgaac ggggggttcg tgcacacaga 5760
ccagcttgga gcgaacgacc tacaccgaac tgagatacct acagcgtgag cattgagaaa 5820
gcgccacgct tcccgaaggg agaaaggcgg acaggtatcc ggtaagcggc agggtcggaa 5880
caggagagcg cacgagggag cttccagggg gaaacgcctg gtatctttat agtcctgtcg 5940
ggtttcgcca cctctgactt gagcgtcgat ttttgtgatg ctcgtcaggg gggcggagcc 6000
tatgaaaaa cgccagcaac gcggcctttt tacggttcct ggccttttgc tggccttttg 6060
ctcacatgtt ctttcctgcg ttatcccctg attctgtgga taaccgtatt accgcctttg 6120
agtgagctga taccgctcgc cgcagccgaa cgaccgagcg cagcgagtca gtgagcgagg 6180
aagcggaaga gcgcccaata cgcaaaccgc ctctccccgc gcgttggccg attcattaat 6240
gcagctggca cgacaggttt cccgactgga aagcgggcag tgagcgcaac gcaattaatg 6300
tgagttagct cactcattag gcaccccagg ctttacactt tatgcttccg gctcgtatgt 6360
tgtgtggaat tgtgagcgga taacaatttc acacaggaaa cagctatgac catgattacg 6420
ccaagcttgc atgcctgcag gtcgactcta g                              6451

<210> SEQ ID NO 4
<211> LENGTH: 3176
<212> TYPE: DNA
<213> ORGANISM: Artificial Sequence
<220> FEATURE:
<223> OTHER INFORMATION: Description of Artificial Sequence: Plasmid
      pLG0082

<400> SEQUENCE: 4
aacctggctt atcgaaatta atacgactca ctatagggag accggcagat ctgatatcat  60
cgatgaattc gagctccacc gcggtggcgg ccgctctaga actagtggat ccaccggttc 120
catggttctc cgtccaaagt tcaatagtca caacgaaaac ggtgctacta ctgcaaaaat 180
aacaacagat tcttcaattc tcggaagctt ctacgtgtgt gcaaaaatt gtgacgacgt 240
caagcgcggc aaactgcggg tttattgcca aaaatgctcg tcaacctctg ttctagtcaa 300
```

-continued

```
atctgaaccc cagaactggt ccgacgttct caaaagcaag agaataccgg cggtctgcga  360
agaatgctgt actccaggtc ttttcgctga attcaagttc aaatgtctag cctgcaacga  420
tccgccgca gctctaactc acgtacgcgg aaattggcaa atgaccgagt gctgtgtttg  480
tgatgggaag gagaaagtga tcttcgacct cggatgcaat catattacat gccaattctg  540
ctgcaggaat tcgatatcaa gcttatcgat accgtcgacc tcgagggggg gcccggtacc  600
caattcgccc tatagtgagt cgtattacgc gcgctcactg gccgtcgttt tacaacgtcg  660
tgactgggaa aaccctggcg ttacccaact taatcgcctt gcagcacatc cccctttcgc  720
cagctggcgt aatagcgaag aggcccgcac cgatccgccc tcccaacagt tgcgcagcct  780
gaatggcgaa tgggacgcgc cctgtagcgg cgcattaagc gcggcgggtg tggtggttac  840
gcgcagcgtg accgctacac ttgccagcgc cctagcgccc gctcctttcg ctttcttccc  900
ttcctttctc gccacgttcg ccggcttccc ccgtcaagct ctaaatcggg gctcccttt   960
agggttccga tttagtgctt tacggcacct cgaccccaaa aaacttgatt agggtgatgg 1020
ttcacgtagt gggccatcgc cctgatagac ggtttttcgc cctttgacgt tggagtccac 1080
gttctttaat agtggactct tgttccaaac tggaacaaca ctcaacccta tctcggtcta 1140
ttcttttgat ttataaggga ttttgccgat ttcggcctat tggttaaaaa atgagctgat 1200
ttaacaaaaa tttaacgcga attttaacaa aatattaacg cttacaattt aggtggcact 1260
tttcggggaa atgtgcgcgg aaccccctatt tgtttatttt tctaaataca ttcaaatatg 1320
tatccgctca tgagacaata accctgataa atgcttcaat aatattgaaa aaggaagagt 1380
atgagtattc aacatttccg tgtcgccctt attccctttt ttgcggcatt ttgccttcct 1440
gttttgctc acccagaaac gctggtgaaa gtaaaagatg ctgaagatca gttgggtgca 1500
cgagtgggtt acatcgaact ggatctcaac agcggtaaga tccttgagag ttttcgcccc 1560
gaagaacgtt ttccaatgat gagcactttt aaagttctgc tatgtggcgc ggtattatcc 1620
cgtattgacg ccgggcaaga gcaactcggt cgccgcatac actattctca gaatgacttg 1680
gttgagtact caccagtcac agaaaagcat cttacggatg gcatgacagt aagagaatta 1740
tgcagtgctg ccataaccat gagtgataac actgcggcca acttacttct gacaacgatc 1800
ggaggaccga aggagctaac cgcttttttg cacaacatgg gggatcatgt aactcgcctt 1860
gatcgttggg aaccggagct gaatgaagcc ataccaaacg acgagcgtga caccacgatg 1920
cctgtagcaa tggcaacaac gttgcgcaaa ctattaactg gcgaactact tactctagct 1980
tcccgcaac aattaataga ctggatggag gcggataaag ttgcaggacc acttctgcgc 2040
tcggcccttc cggctggctg gtttattgct gataaatctg gagccggtga gcgtgggtct 2100
cgcggtatca ttgcagcact ggggccagat ggtaagccct cccgtatcgt agttatctac 2160
acgacgggga gtcaggcaac tatggatgaa cgaaatagac agatcgctga ataggtgcc 2220
tcactgatta agcattggta actgtcagac caagtttact catatatact ttagattgat 2280
ttaaaacttc attttaatt taaaaggatc taggtgaaga tccttttga taatctcatg 2340
accaaaatcc cttaacgtga gttttcgttc cactgagcgt cagacccgt agaaaagatc 2400
aaaggatctt cttgagatcc ttttttctg cgcgtaatct gctgcttgca acaaaaaaa 2460
ccaccgctac cagcggtggt ttgtttgccg gatcaagagc taccaactct ttttccgaag 2520
gtaactggct tcagcagagc gcagatacca aatactgtcc ttctagtgta gccgtagtta 2580
ggccaccact tcaagaactc tgtagcaccg cctacatacc tcgctctgct aatcctgtta 2640
ccagtggctg ctgccagtgg cgataagtcg tgtcttaccg ggttggactc aagacgatag 2700
ttaccggata aggcgcagcg gtcgggctga acggggggt cgtgcacaca gcccagcttg 2760
gagcgaacga cctacaccga actgagatac ctacagcgtg agctatgaga aagcgccacg 2820
cttcccgaag ggagaaaggc ggacaggtat ccggtaagcg gcagggtcgg aacaggagag 2880
cgcacgaggg agcttccagg gggaaacgcc tggtatcttt atagtcctgt cgggtttcgc 2940
cacctctgac ttgagcgtcg attttgtga tgctcgtcag ggggcggag cctatggaaa 3000
aacgccagca acgcggcctt tttacggttc ctggccttt tgctcacatg 3060
ttcttcctg cgttatcccc tgattctgtg ataaccgta ttaccgcctt tgagtgagct 3120
gataccgctc gccgcagccg aacgaccgag cgcagcgagt cagtgagcga ggaagc     3176
```

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Primer
      RB850

<400> SEQUENCE: 5
gggccgcggc atgcgaatac aatgacgtaa gcgacgtgg                          39

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Primer
      RB851

<400> SEQUENCE: 6
cccgtcgact catcagacat gcttcatgag agc                                33

<210> SEQ ID NO 7
<211> LENGTH: 32
<212> TYPE: DNA

```
<213> ORGANISM: Artificial Sequence
<220> FEATURE:
<223> OTHER INFORMATION: Description of Artificial Sequence: Primer
      RB853

<400> SEQUENCE: 7
gggccgcggt tcgaatttga agctcgctgc gt                                32

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Primer
      RB916

<400> SEQUENCE: 8
cgcccgggag ctcgtcgacc tattaaacca atggtcccat tgacactc               48

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer
      1-RNA1

<400> SEQUENCE: 9
cagacaaacc atggttctcc                                              20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer
      1-RNA2

<400> SEQUENCE: 10
cttactctgc agcagaattg g                                            21

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer
      RB759

<400> SEQUENCE: 11
cccggctgca gctcaattat tctagtaagc                                   30

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Primer
      RB110

<400> SEQUENCE: 12
gtctccatgg atccgaattc tgaaacgttc aaataac                           37
```